United States Patent
Ahn et al.

(10) Patent No.: US 11,498,976 B2
(45) Date of Patent: Nov. 15, 2022

(54) VIRAL COMPLEX COMPRISING SHRNA AND ANTI-EPCAM ANTIBODY AND USES THEREOF

(71) Applicant: KOREA INSTITUTE OF SCIENCE AND TECHNOLOGY, Seoul (KR)

(72) Inventors: Hyung Jun Ahn, Seoul (KR); Sungjin Lee, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 241 days.

(21) Appl. No.: 16/878,672

(22) Filed: May 20, 2020

(65) Prior Publication Data

US 2020/0369780 A1 Nov. 26, 2020

(30) Foreign Application Priority Data

May 20, 2019 (KR) .......................... 10-2019-0059007

(51) Int. Cl.
| | | |
|---|---|---|
| *C07H 21/04* | (2006.01) | |
| *C07K 16/30* | (2006.01) | |
| *A61P 35/00* | (2006.01) | |
| *C12N 15/86* | (2006.01) | |

(52) U.S. Cl.
CPC .............. *C07K 16/30* (2013.01); *A61P 35/00* (2018.01); *C12N 15/86* (2013.01); *C12N 2310/122* (2013.01)

(58) Field of Classification Search
None
See application file for complete search history.

(56) References Cited

PUBLICATIONS

Brown, Taylor C., Narendra V. Sankpal, and William E. Gillanders. "Functional implications of the dynamic regulation of EpCAM during epithelial-to-mesenchymal transition." Biomolecules 11.7 (2021): 956.*
Oh YK. et al., siRNA delivery systems for cancer treatment, Adv Drug Deliver Reviews 61, 2009, 850-862.
Stilwell JL. et al., Adeno-Associated Virus Vectors for Therapeutic Gene Transfer, BioTechniques 2003, vol. 34, No. 1, 148-150.
Stone D. et al., Biodistribution and Safety Profile of Recombinant Adeno-Associated Virus Serotype 6 Vectors following Intravenous Delivery, J. Virol., Aug. 2008, vol. 82, No. 15, 7711-7715.
S. Michael Rothenberg, et al., Modeling oncogene addiction using RNA interference, PNAS, 2008 vol. 105(34), pp. 12480-12484.
H J Haisma, et al., Tumor-specific gene transfer via an adenoviral vector targeted to the pan-carcinoma antigen EpCAM, Gene Therapy (1999) 6, pp. 1469-1474.
Office Action issued in KR 10-2019-0059007 by the Korean Intellectual Patent Office dated Sep. 15, 2020 for the above-identified U.S. application.

* cited by examiner

*Primary Examiner* — Kimberly Chong
(74) *Attorney, Agent, or Firm* — Cantor Colburn LLP

(57) ABSTRACT

The present invention relates to a viral complex comprising a viral vector capable of delivering shRNA that suppresses an expression of epidermal growth factor receptor (EGFR) to a cell and an anti-epithelial cell adhesion molecule (EpCAM) antibody conjugated to the viral vector, a pharmaceutical composition for preventing or treating cancer, comprising the viral complex, and a method for treating cancer, comprising administering the viral complex or the pharmaceutical composition to a subject in which a cancer disease has occurred and overexpressing EpCAM. The anti-EpCAM antibody-AAV2/shEGFR complex provided in the present invention significantly reduces the expression level of EGFR in tumor cells overexpressing EpCAM without inducing an immune response in vivo, thereby inducing death of tumor cells, and thus, it can be widely utilized in more effective and safe cancer treatment.

7 Claims, 12 Drawing Sheets
(9 of 12 Drawing Sheet(s) Filed in Color)

Specification includes a Sequence Listing.

[FIG. 1]
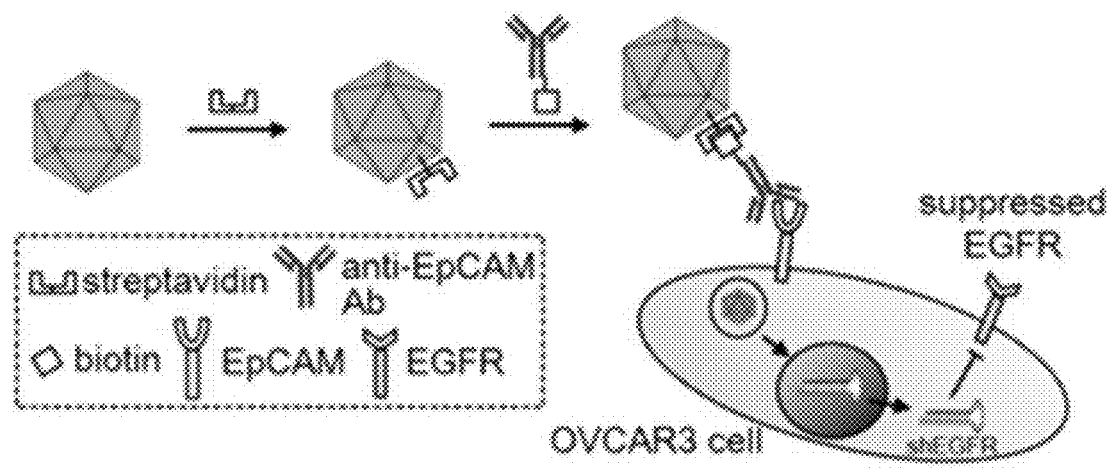
[FIG. 2A]
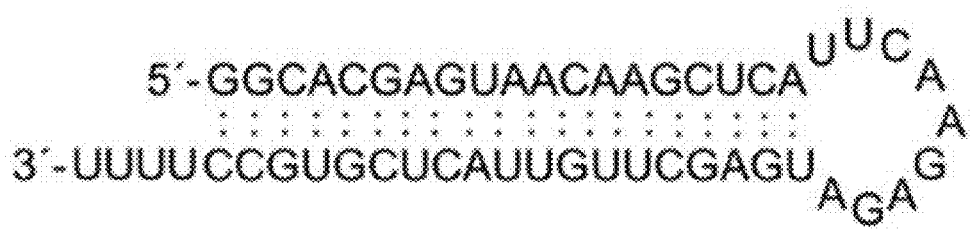

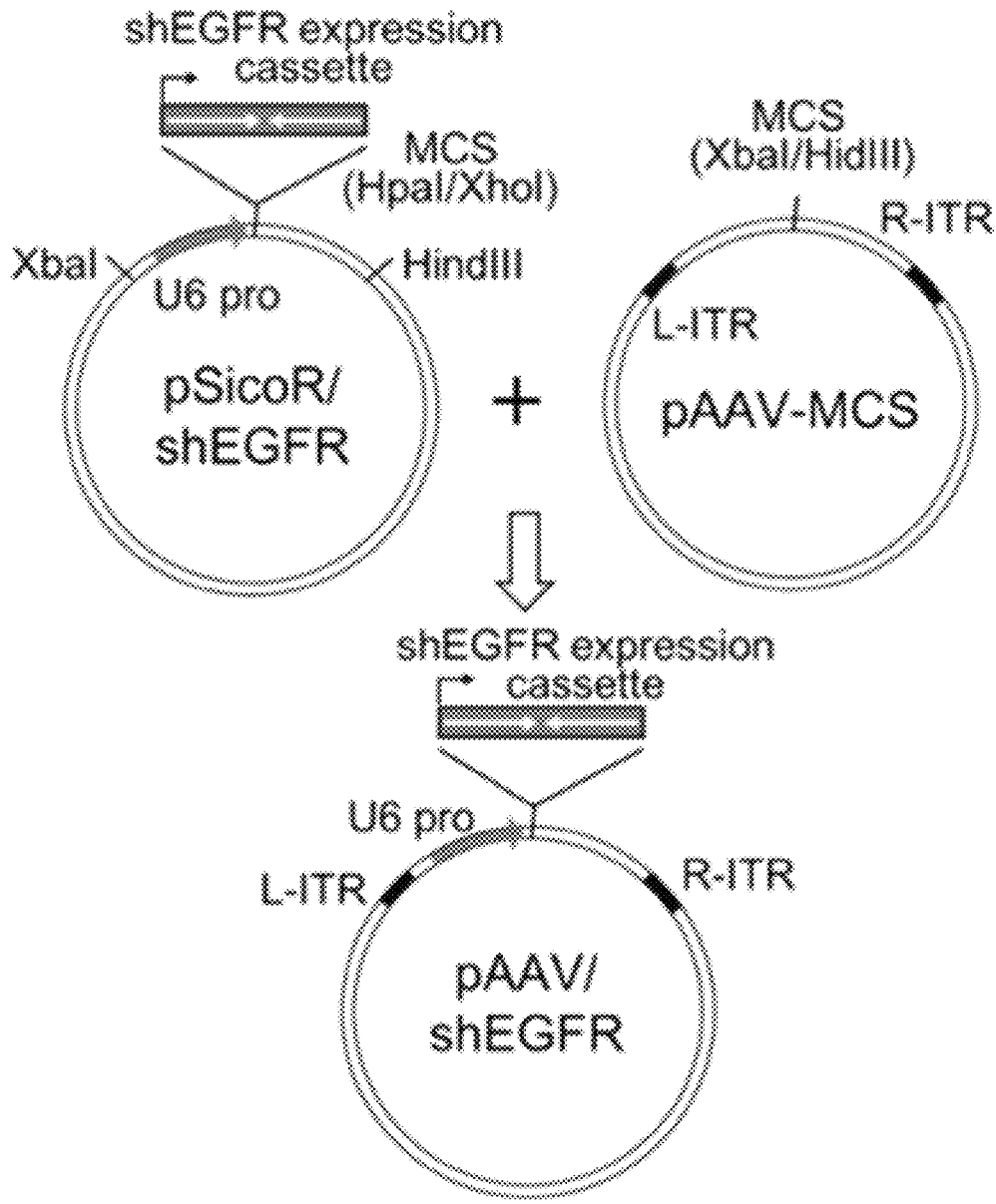
[FIG. 2B]

[FIG. 3A]
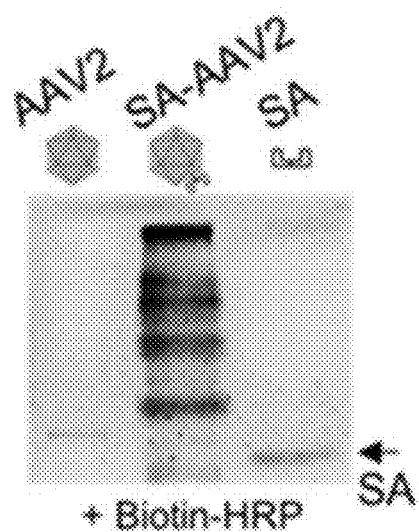
[FIG. 3B]
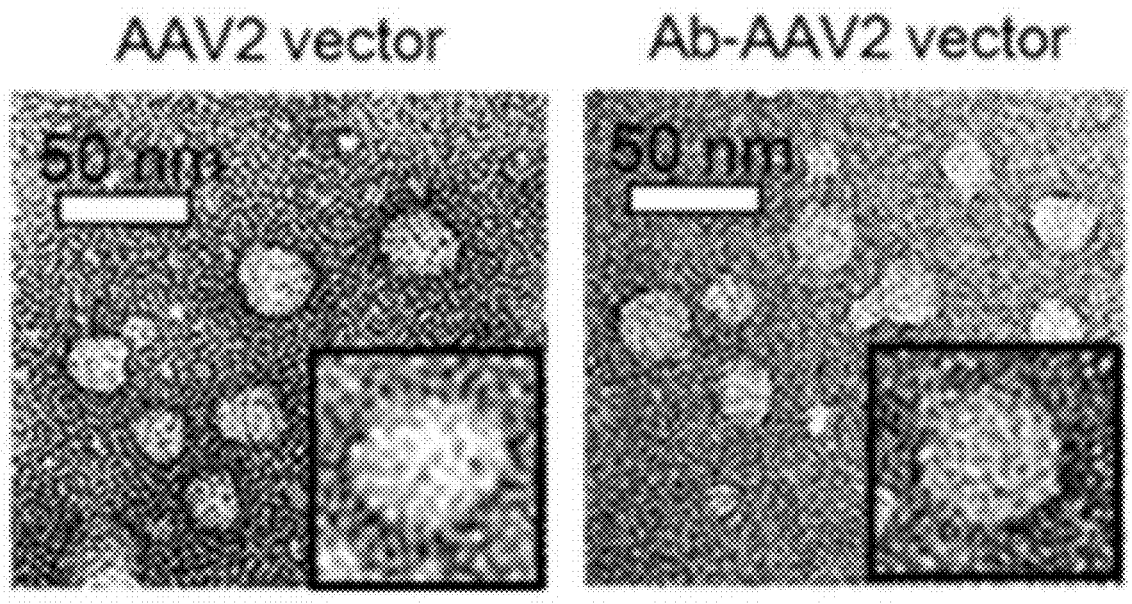

[FIG. 4A]
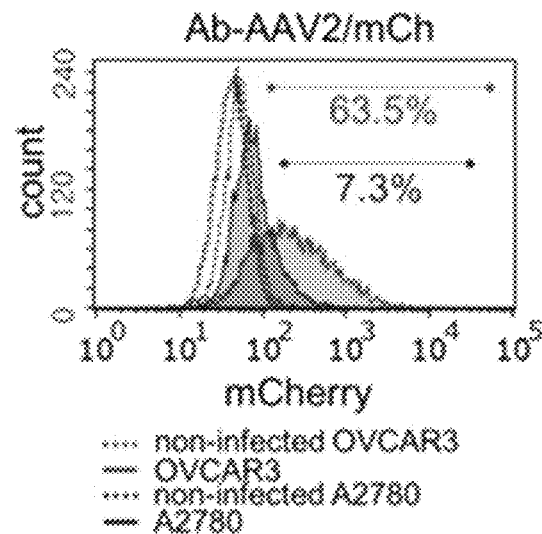
[FIG. 4B]
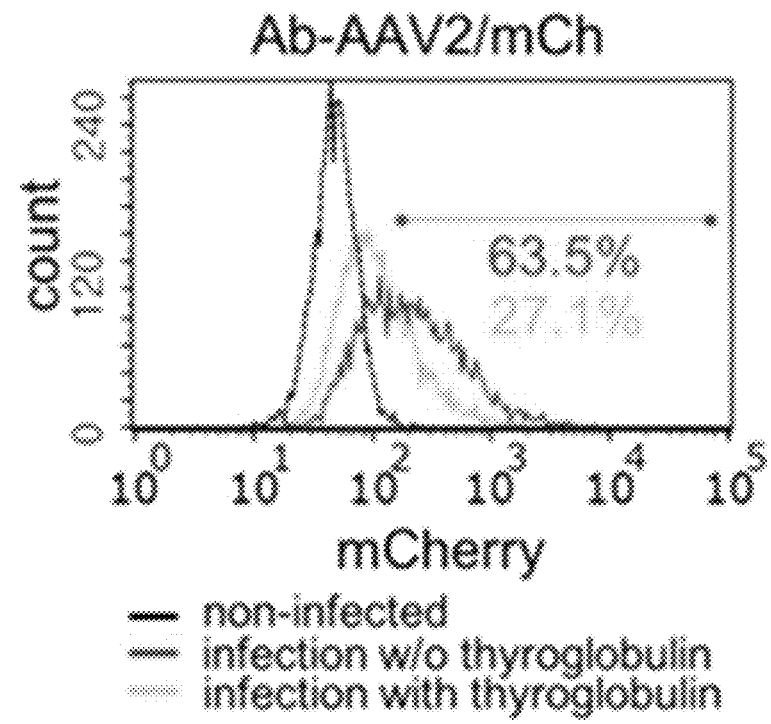

[FIG. 4C]
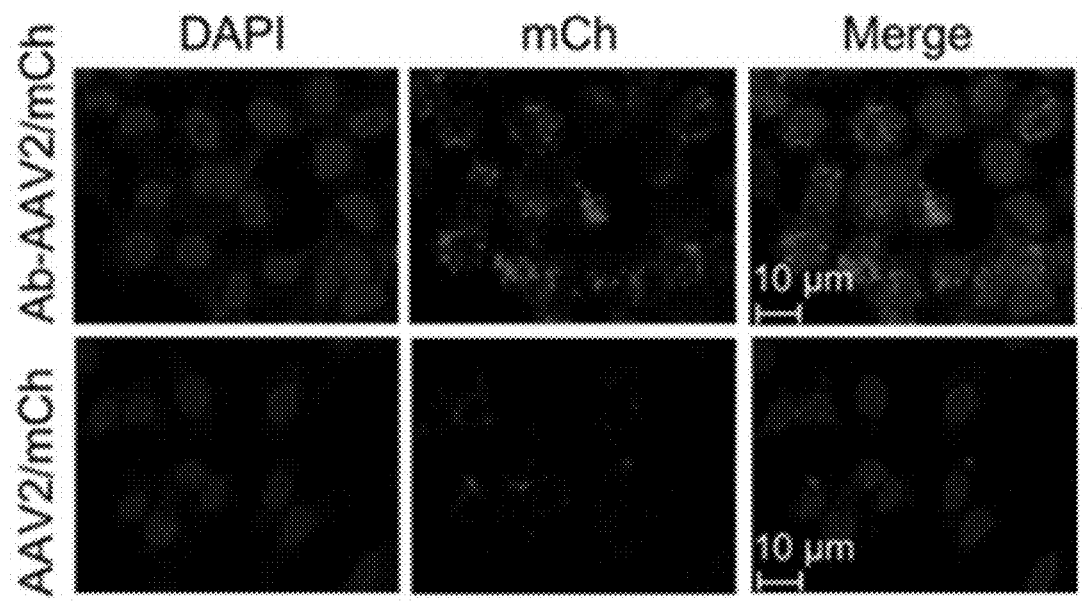
[FIG. 5A]
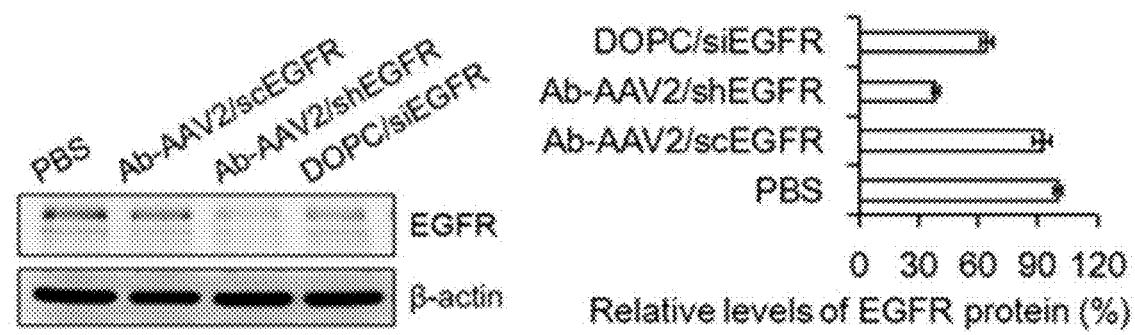

[FIG. 5B]
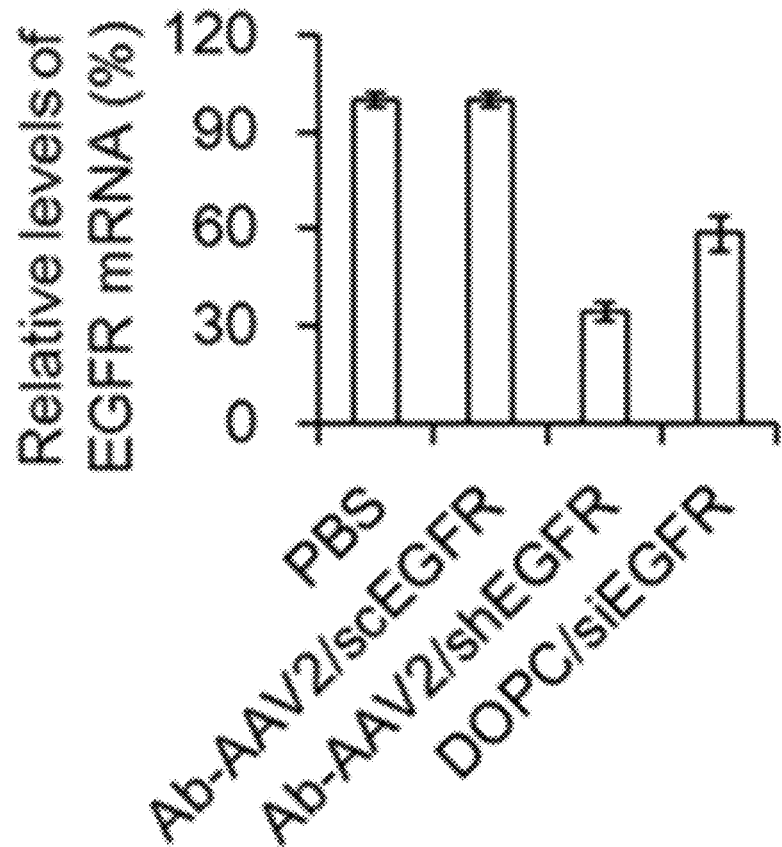
[FIG. 5C]
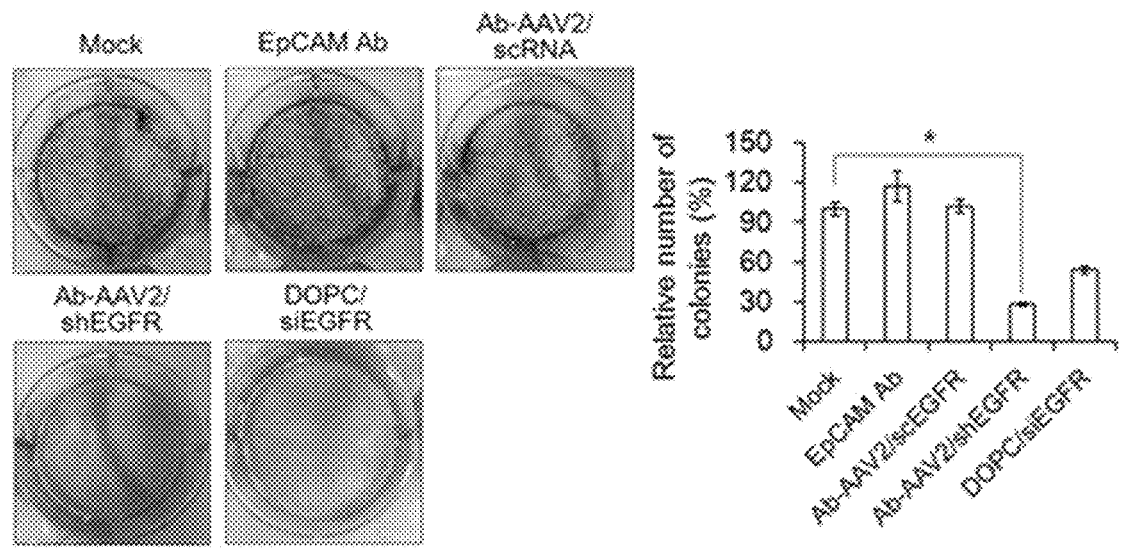

[FIG. 5D]
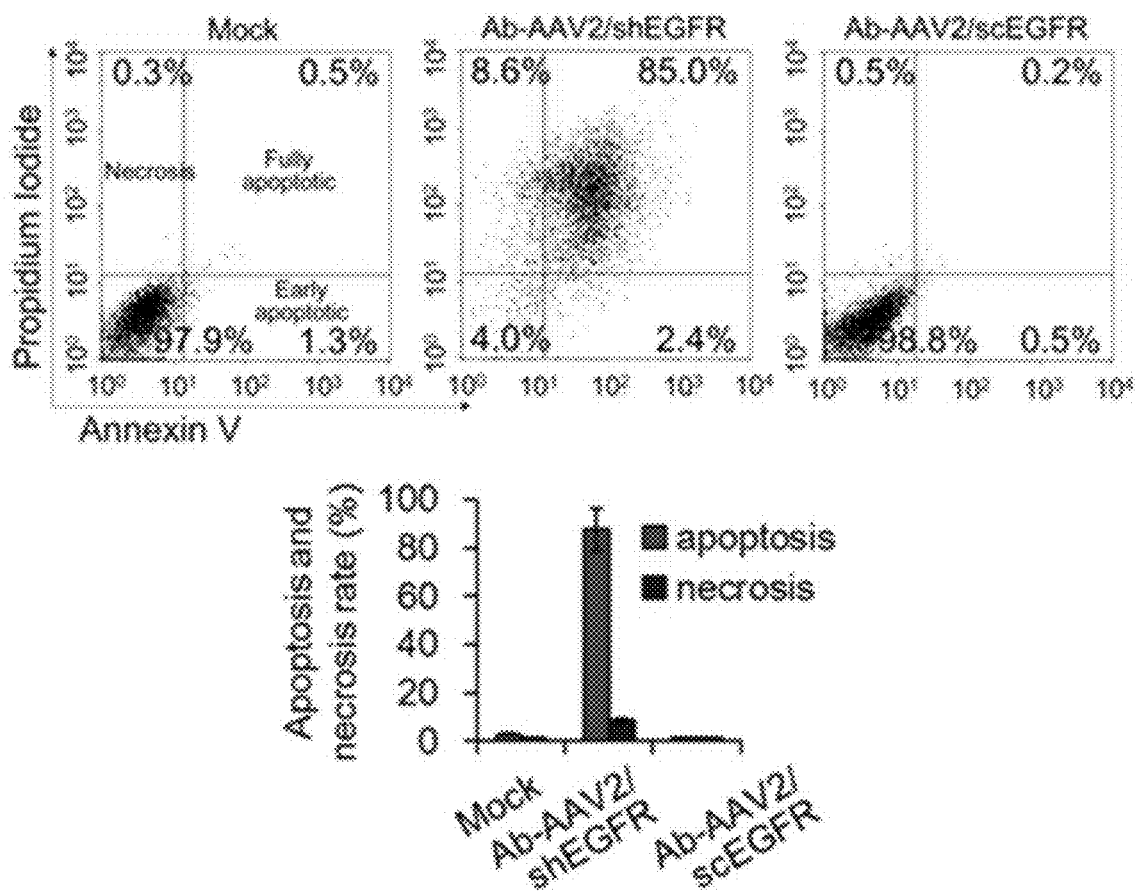

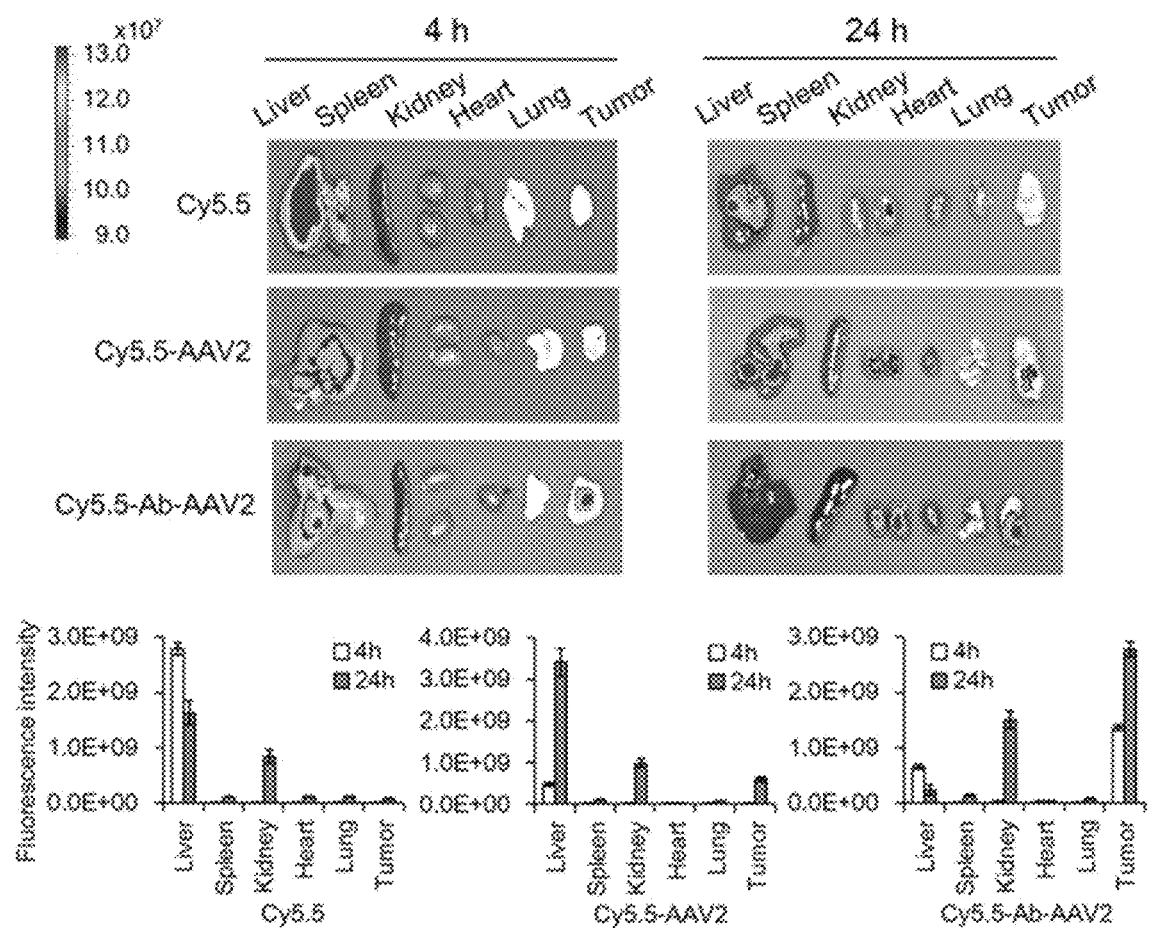
[FIG. 6A]

[FIG. 6B]
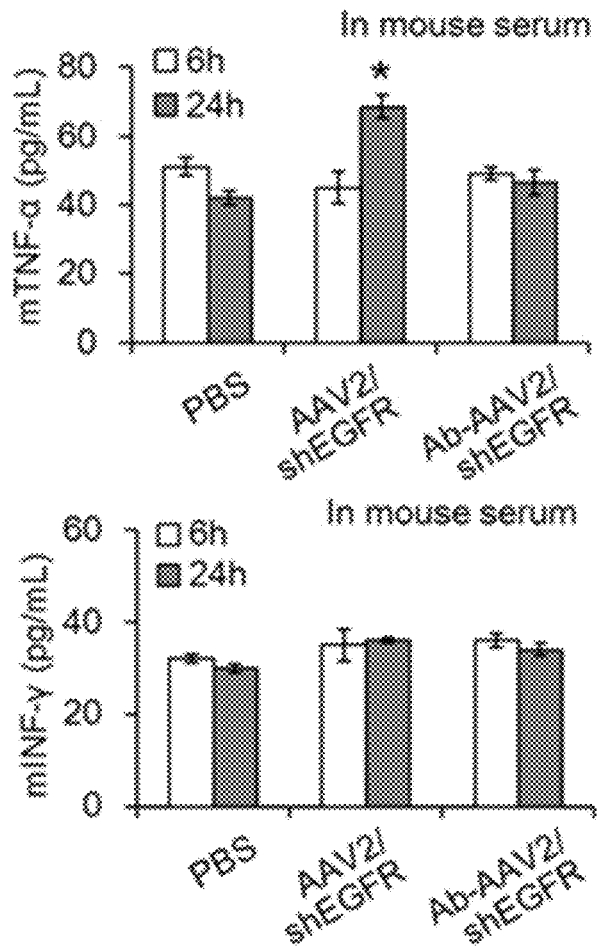
[FIG. 6C]
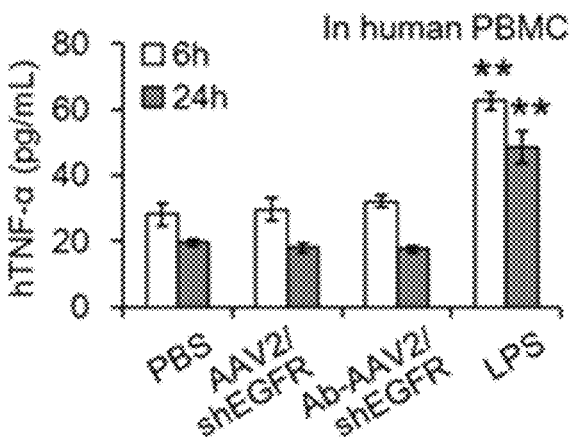

[FIG. 7A]
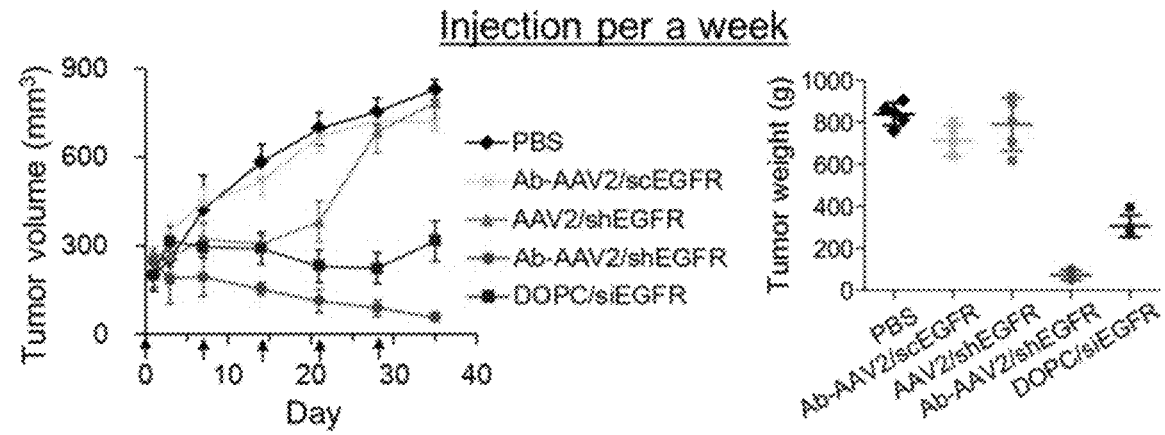
[FIG. 7B]
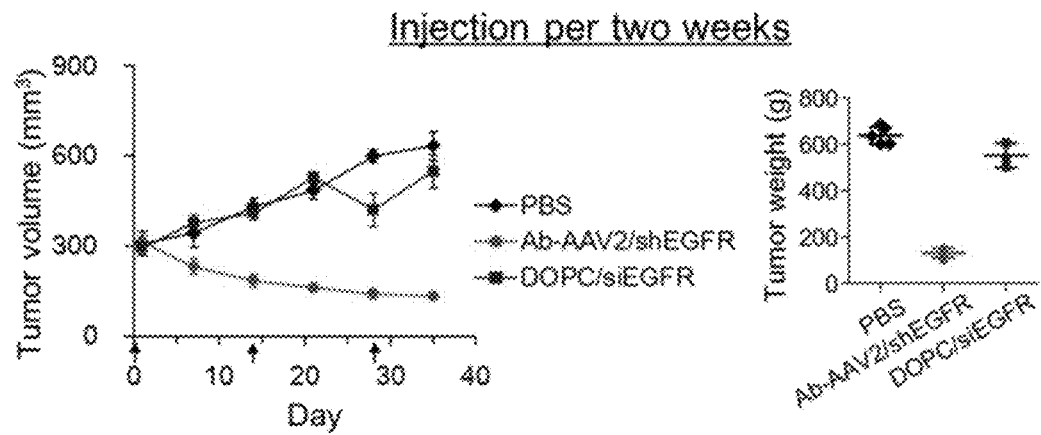
[FIG. 7C]
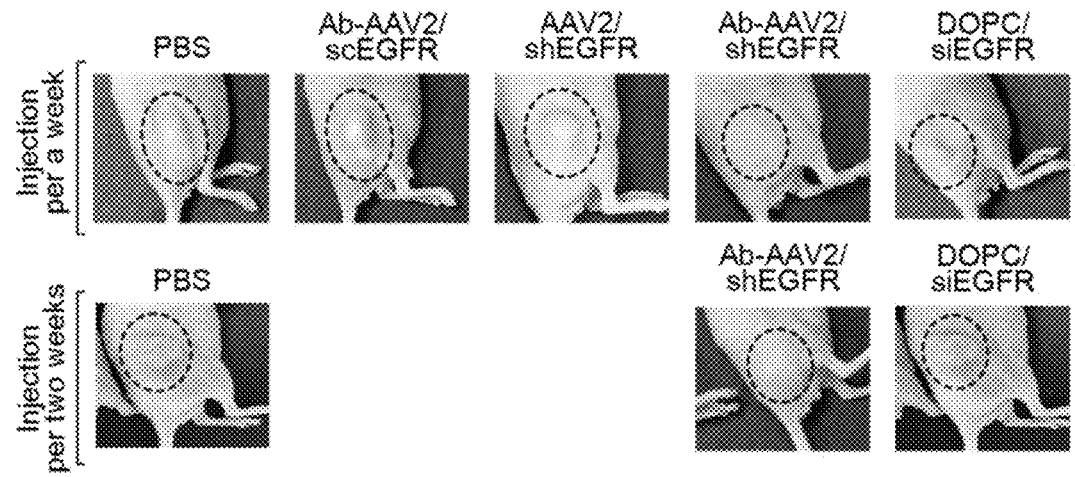

[FIG. 7D]
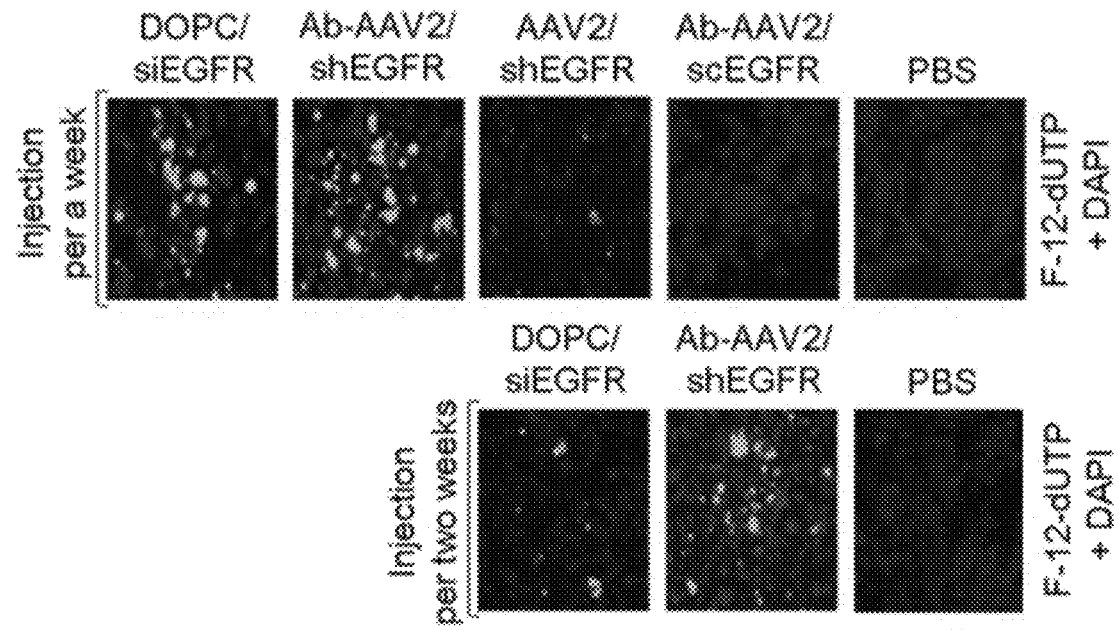
[FIG. 7E]
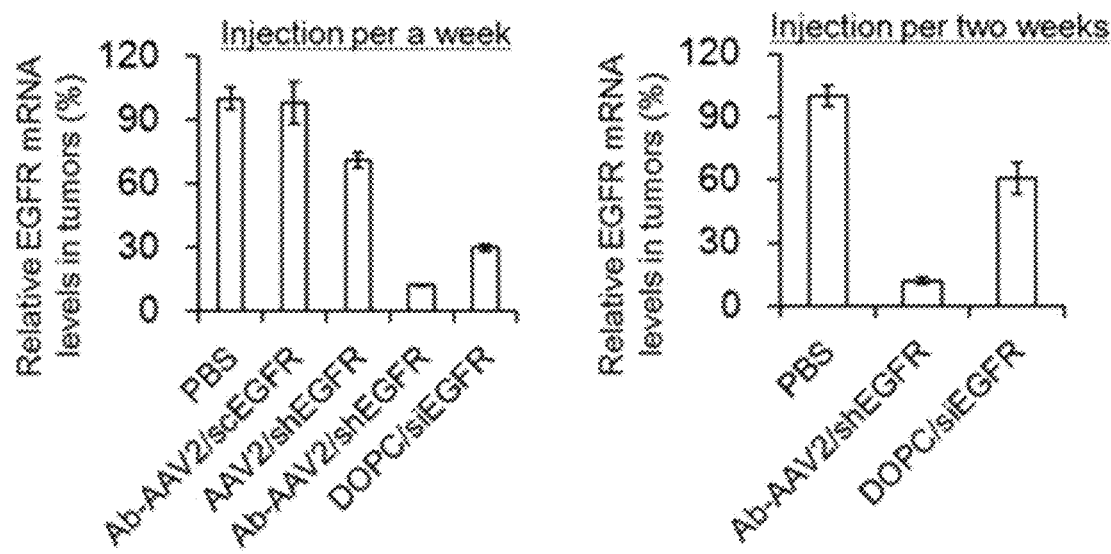

[FIG. 7F]
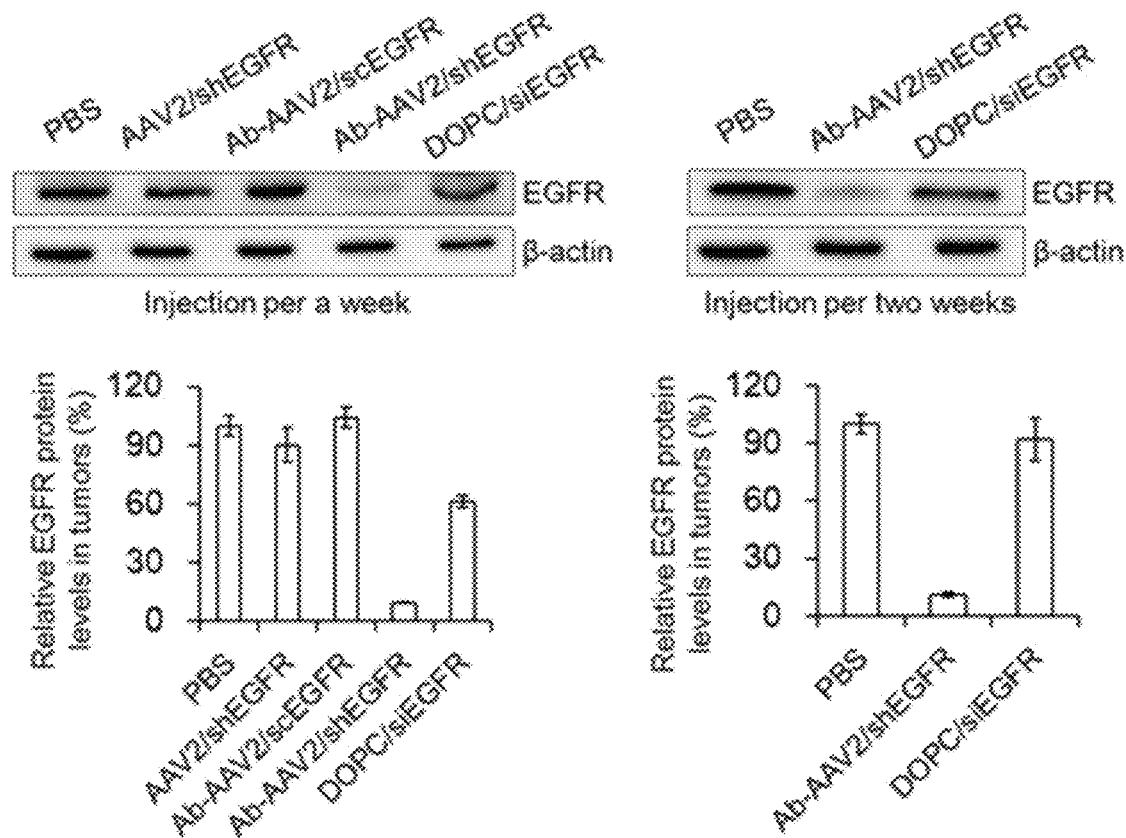
[FIG. 7G]
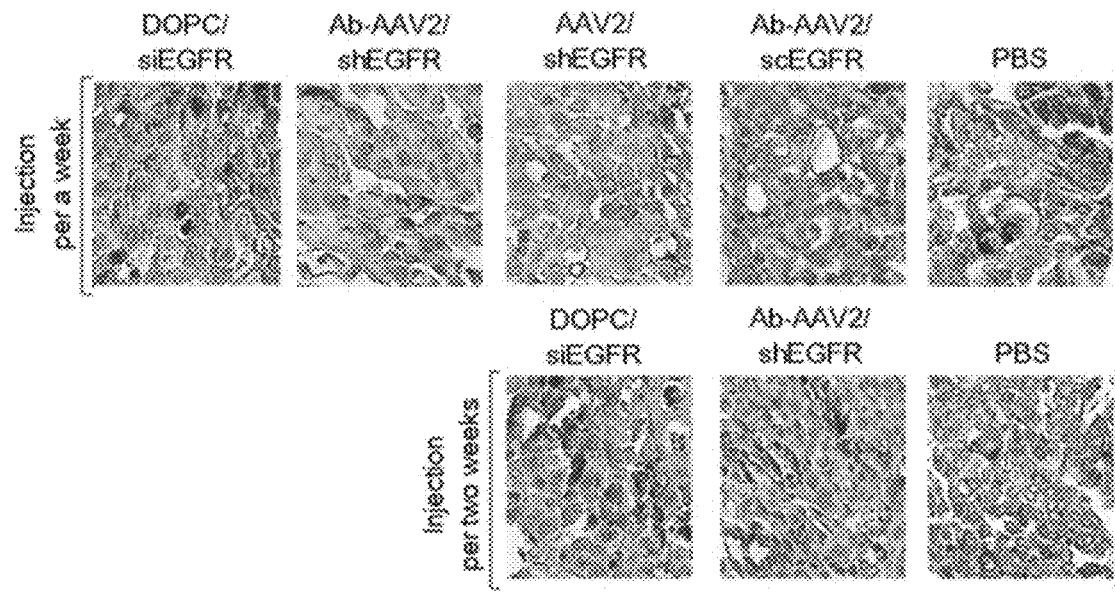

SEQUENCE LISTING

```
<160> NUMBER OF SEQ ID NOS: 5

<210> SEQ ID NO 1
<211> LENGTH: 64
<212> TYPE: DNA
<213> ORGANISM: Artificial Sequence
<220> FEATURE:
<223> OTHER INFORMATION: shRNA

<400> SEQUENCE: 1
gttaacggca cgagtaacaa gctcattcaa gagatgagct tgttactcgt gccttttct      60 cgag                                                                  64

<210> SEQ ID NO 2
<211> LENGTH: 64
<212> TYPE: DNA
<213> ORGANISM: Artificial Sequence
<220> FEATURE:
<223> OTHER INFORMATION: shRNA

<400> SEQUENCE: 2
ctcgagaaaa aggcacgagt aacaagctca tctcttgaat gagcttgtta ctcgtgccgt      60
taac                                                                  64

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
tgcccatgag aaatttacag g                                               21

<210> SEQ ID NO 4
<211> LENGTH: 22
<212> TYPE: DNA
<213> ORGANISM: Artificial Sequence
<220> FEATURE:
```

```
<223> OTHER INFORMATION: shRNA

<400> SEQUENCE: 4
atgttgctga gaaagtcact gc                                              22

<210> SEQ ID NO 5
<211> LENGTH: 51
<212> TYPE: RNA
<213> ORGANISM: artificial sequence
<220> FEATURE:
<223> OTHER INFORMATION: shRNA

<400> SEQUENCE: 5
ggcacgagua acaagcucau ucaagagaug agcuuguuac ucgugccuuu u              51
```

VIRAL COMPLEX COMPRISING SHRNA AND ANTI-EPCAM ANTIBODY AND USES THEREOF

CROSS-REFERENCE TO RELATED APPLICATION

This application claims priority to Korean Patent Application No. 10-2019-0059007 filed on May 20, 2019 in the Korean Intellectual Property Office, the disclosure of which is incorporated herein in its entirety by reference.

SEQUENCE LISTING

A Sequence Listing, incorporated herein by reference, is submitted in electronic form as an ASCII text file, created May 11, 2020, size 4 kB. and named "8JK0362.TXT".

TECHNICAL FIELD

The present invention relates to a viral complex comprising shRNA and anti-EpCAM antibody and uses thereof, and more specifically the present invention relates to a viral complex comprising a viral vector similar to AAV2 that can deliver shRNA suppressing the expression of epidermal growth factor receptor (EGFR) to a cell and an anti-epithelial cell adhesion molecule (EpCAM) antibody conjugated to the viral vector, a pharmaceutical composition for preventing or treating cancer comprising the viral complex, and a method for treating cancer comprising administering the viral complex or pharmaceutical composition that can selectively deliver a viral vector comprising EGFR shRNA to cancer tissue, to a subject in which a cancer disease has occurred overexpressing EpCAM.

BACKGROUND ART

RNA interference (RNAi) refers to a phenomenon in which double strand RNA consisting of sense RNA having a sequence homologous to the mRNA of a target gene and antisense RNA having a sequence complementary thereto is introduced to a cell, etc. to selectively induce degradation of the mRNA of a target gene or suppress the expression of a target gene. While RNAi was initially observed in nematodes, it is now observed to be a well-preserved life phenomenon in various organisms such as yeast, insects, plants, and humans, etc. Substances that induce such RNAi are known to be small interference RNA (siRNA), microRNA (miRNA), etc., and among these, siRNA that can be artificially synthesized is in the form of an RNA double-helix strand consisting of about 20 to 30 nucleotides. When expressed in the cell, it degrades mRNA whose base sequence is complementary thereto and suppresses the expression of a related gene. siRNA has a therapeutic effect against disease, and has been in the spotlight as an effective means of controlling a targeted life process due to easy preparation and high target selectivity.

Accordingly, methods for treating various diseases such as cancer, viral infections, autoimmune disease, neurodegenerative diseases, etc. using siRNA are being studied, and for example, the development of therapeutic agents for senile macular degeneration (bevasiranib; Opko Health Inc., Miami, Fla., USA; phase 3 clinical trial), and respiratory syncytial virus infection (ALN-RSV01; Alnylam, Cambridge, Mass., USA; phase 2 clinical trial) is in progress at clinical levels (Melnikova I *Nat Rev Drug Discov* 2007, 6, 863-864). In addition, siRNA is used in the method of treating cancer using a nanoparticle polymer based on cyclodextrin targeting transferrin (CALAA-01; Calando Pharmaceuticals, Pasadena, Calif., USA; phase 1 clinical trial) (Oh Y K. et al., *Adv Drug Deliver Rev* 2009, 61, 850-862).

However, the method of suppressing gene expression using siRNA has a problem that its duration is as short as about 2 to 4 days, and this is because siRNA is easily degraded by various nucleases in the cytoplasm, and when cell division occurs, the concentration of siRNA is diluted. This short persistence problem not only raises the problem of having to frequently inject synthetic siRNA, but also there is a disadvantage that the efficiency is very low because the duration is too short to suppress the expression of a target protein having a relatively long half-life.

Efforts to improve existing gene silencing persistence have led to the development of viral vectors. In the case of retroviral vectors such as adenovirus and lentivirus in which persistence of gene silencing can occur for a long time (for example, several weeks), in spite of their excellent persistence, it has been pointed out that in vivo stability cannot be guaranteed due to in vivo immune responses, viral gene insertion into the host genome in the body of an infected host, and the induction of mutations, thereby having limitations in human application.

Meanwhile, adeno-associated virus (AAV) is known to be advantageous for human application due to the differentiation from the above-mentioned retrovirus (Stilwell J L. et al., *Bio Techniques* 2003, 34, 148-150). AAV can minimize the immune responses in the body, and whereas the existing viruses have limitations in which the infection efficiency is high only in dividing cells and the infection efficiency is low in non-dividing cells, AAV shows high infection efficiency in non-dividing cells too. In addition, unlike adenovirus, it does not have harmful pathogenicity while not damaging T cells, and does not replicate in infected cells. In addition, there is no inherent risk of human application because viral gene insertion does not occur in the genome of the infected host.

However, since host tropism of AAV is very extensive, there is a problem that it is difficult to selectively deliver to a specific diseased tissue. This is because the AAV has a mechanism of mainly binding to a heparin sulfate proteoglycan (HSPG) receptor and penetrating into the cell, and HSPG receptors are known to be widely distributed in numerous tissues and cell types in vivo. In addition, when injected intravenously into a mouse or a non-human primate, AAV accumulates mainly in the liver or spleen, and thus has a limitation that selective gene transfer to a desired diseased tissue is impossible. As a result, for the application of anticancer agents that should selectively act on tumor, the limitations of such natural tropism should be first solved (Stone D. et al., *J. Virol.* 2008, 82, 7711-7715). Under this background, efforts have been made to develop a method to more effectively deliver shRNA to a target cell using AAV, and the present inventors completed the present invention by confirming that when a viral complex is used that comprises a viral vector capable of delivering shRNA to a cell and an anti EpCAM antibody conjugated to the viral vector, shRNA can be effectively delivered to a target cell.

DISCLOSURE

Technical Problem

The main object of the present invention is to provide a viral complex, comprising a viral vector capable of delivering shRNA that suppresses an expression of epidermal growth factor receptor (EGFR) to a cell and an anti-epithelial cell adhesion molecule (EpCAM) antibody conjugated to the viral vector.

Another object of the present invention is to provide a pharmaceutical composition for preventing or treating cancer, comprising the viral complex.

Another object of the present invention is to provide a method for treating cancer, comprising administering the viral complex, capable of selectively delivering a viral vector comprising EGFR shRNA to a cancer tissue, to a subject, in which a cancer disease has occurred overexpressing EpCAM.

Technical Solution

To achieve the above-mentioned objects, an aspect of the present invention is to provide a viral complex, comprising a viral vector capable of delivering shRNA that suppresses an expression of epidermal growth factor receptor (EGFR) to a cell and an anti-epithelial cell adhesion molecule (EpCAM) antibody conjugated to the viral vector.

As used herein, the term "epidermal growth factor receptor (EGFR)" refers to a receptor protein having the form of a transmembrane protein for the epidermal growth factor (EGF) family of extracellular protein ligands. When the EGFR is overexpressed due to mutation, it is known that it can cause various types of cancer disease. Moreover, EGFR has also been reported to be associated to the pathogenesis of Alzheimer's disease. According to recent studies, it has been reported that when the expression of EGFR is suppressed, the prognosis of cancer diseases can be improved.

As used herein, the term "small hairpin RNA or short hairpin RNA (shRNA)" refers to RNA having the structure of a small hair pin that can suppress the expression of genes, by binding to mRNA and inhibiting its translation. When the shRNA is introduced into the cell, it is cleaved by intracellular enzymes to form siRNA, and the siRNA thus formed binds to mRNA having a complementary sequence thereto to decompose the mRNA.

In the present invention, the shRNA may be interpreted as shRNA that suppresses the expression of EGFR, and as an example, it can be interpreted as shRNA consisting of SEQ ID NOs.: 1 and 2.

```
                                              (SEQ ID NO.: 1)
5'-GTTAAC(GGCACGAGTAACAAGCTCA)TTCAAGAGA(TGAGCTTGTT

ACTCGTGCC)TTTTTCTCGAG-3'

(SEQ ID NO.: 2)
5'-CTCGAGAAAAA(GGCACGAGTAACAAGCTCA)TCTCTTGAA(TGAGC

TTGTTACTCGTGCC)GTTAAC-3'
```

As used herein, the term "viral vector" refers to a gene delivery means for infecting a cell and delivering a gene present in the virus into the cell by modifying a wild-type virus and without causing toxicity in vivo.

As the viral vector, viruses such as retrovirus, adenovirus, adeno-associated virus, herpes simplex virus, etc. may be used. In the embodiment of the present invention, detoxified adeno-associated virus was used as the viral vector.

As used herein, the term "epithelia cell adhesion molecule (EpCAM) antibody" refers to an antibody protein that specifically binds to the EpCAM.

As used herein, the term "epithelial cell adhesion molecule (EpCAM)" refers to a type of cell adhesion molecules present in epithelial tissue and showing specific adhesion to homologous receptors.

As used herein, the term "cell adhesion molecule (CAM)" refers to a term that collectively refers to molecules such as fibronectin, collagen, laminine, etc. that form an extracellular matrix and receptors present on the cell surface containing the molecules.

Among them, cadherin, neural cell adhesion molecule, etc. show specific adhesion to homologous receptors, but it is known that most cell adhesion molecules except these also exhibit adhesion activity to heterologous adhesion molecules.

In the present invention, as the EpCAM is overexpressed on the surface of a cancer cell, it is used as a medium that the viral complex provided in the present invention is targeted to a cancer cell.

As used herein, the term "viral complex" refers to a molecule in the form where a viral vector containing a gene of interest and an antibody capable of specifically binding to surface antigens of a target cell are combined, and it shows specificity for a target cell by the antibody and can deliver a target gene to the target cell by the viral vector.

In the present invention, the viral complex may be interpreted as a viral complex in the form where an anti-EpCAM antibody is conjugated to a viral vector capable of delivering shRNA that suppresses the expression of EGFR to a cell. In particular, it is in the form where an anti-EpCAM antibody is conjugated to a viral vector such that the viral vector comprising EGFR shRNA can be selectively delivered to a tissue in which a target disease is induced such as cancer tissue. Since EpCAM is overexpressed on the cell surface of cancer tissues, due to the overexpressed EpCAM and anti-EpCAM antibody conjugated to the viral complex, the viral complex specifically binds to cancer cells constituting cancer tissue, and infects the cancer cells with EGFR shRNA resulting in inhibiting the growth of cancer cells and killing cancer cells.

The viral complex provided in the present invention may be prepared by binding streptavidin to an adeno-associated virus comprising a gene encoding shRNA that suppresses the expression of EGFR, and conjugating an anti-EpCAM antibody where a biotin is bound thereto. The viral complex thus prepared specifically binds to a target cell overexpressing EpCAM on its surface and delivers shRNA that suppresses the expression of EGFR into the target cell, thereby effectively suppressing the expression of EGFR in the target cell. This overall process is illustrated in FIG. 1.

According to an embodiment of the present invention, the viral complex of the present invention shows a characteristic of specifically binding to and targeting a cancer cell overexpressing EpCAM on its surface by an anti-EpCAM included therein (FIGS. 4a to 4c). In addition, by the nature of the viral vector included in the viral complex, it is possible to effectively suppress the expression of EGFR in a target cell, by delivering the shRNA included therein through the cell membrane of a target cell into the cell (FIGS. 5a and 5b); suppress the formation of a colony of a target cell thereby (FIG. 5c); and induce the death of a target cell (FIG. 5d). Such viral complexes can exhibit the above-mentioned effects at the cellular level as well as in vivo (FIG. 6A).

According to another embodiment of the present invention, while the viral complex of the present invention may be expected to induce an immune response in vivo due to the virus contained therein, surprisingly, it was confirmed that no immune response was induced in vivo (FIGS. 6b and 6c).

Another aspect of the present invention is to provide a pharmaceutical composition for preventing or treating cancer, comprising the viral complex.

Here, the "viral complex" is the same as described above.

In the present invention, the viral complex may be used to prepare a pharmaceutical composition, and specifically, a pharmaceutical composition for preventing or treating cancer can be provided.

In order to use as a pharmaceutical composition for cancer treatment, the viral complex to be delivered in the present invention can be used as an active ingredient of the pharmaceutical composition for preventing or treating cancer.

Moreover, components having additional anticancer activity other than the viral complex of the present invention can be used to further improve the efficacy of preventing of treating cancer.

As used herein, the term "prevention" refers to all activities that inhibit or delay the onset of cancer by administration of the pharmaceutical composition according to the present invention.

As used herein, the term "treatment" refers to all activities that ameliorate or advantageously change the symptoms of a subject that is suspicious for the occurrence of cancer or the occurrence of cancer is confirmed by administration of the pharmaceutical composition.

The pharmaceutical composition provided by the present invention may be used for preventing or treating cancer, and while the cancer that is the target of such prevention or treatment is not particularly limited as long as EpCAM is overexpressed on its surface, examples may be pancreatic cancer, breast cancer, prostate cancer, brain tumor, head and neck carcinoma, melanoma, myeloma, leukemia, lymphoma, liver cancer, gastric cancer, colon cancer, bone cancer, uterine cancer, ovarian cancer, rectal cancer, esophageal cancer, small intestine cancer, anal muscle cancer, colon cancer, fallopian tube carcinoma, endometrial carcinoma, cervical carcinoma, vaginal carcinoma, vulvar carcinoma, Hodgkin's disease, bladder cancer, kidney cancer, ureter cancer, renal cell carcinoma, renal pelvic carcinoma, central nervous system tumor, etc., and as another example, it may be ovarian cancer.

According to an embodiment of the present invention, when the viral complex of the present invention is administered to an animal model of cancer, the volume and weight of cancer tissues are drastically reduced (FIGS. 7a and 7b, and the volume reduction of these cancer tissues can be sufficiently confirmed by the appearance of an animal model (FIG. 7c), and in fact, it was confirmed that the apoptosis was actively progressed in the cancer tissue (FIG. 7d). Such anticancer activity was confirmed to be due to a decrease in the expression of EGFR in the cells of cancer tissue by the viral complex of the present invention (FIGS. 7e to 7g).

In this regard, since the viral complex of the present invention exhibits anticancer activity by specifically acting on cancer tissues in vivo, it has been analyzed to exhibit effective anticancer activity at least for cancer diseases in which EpCAM is overexpressed.

As used herein, the term "pharmaceutical composition" refers to a composition prepared for the purpose of preventing or treating a disease, and it can be formulated and used in various forms according to conventional methods.

The pharmaceutical composition of the present invention may further comprise a pharmaceutically acceptable carrier, excipient, or diluent, and the carrier may include a non-naturally occurring carrier.

More specifically, as a carrier, excipient, and diluent that can be included in the pharmaceutical composition, examples include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, polycaprolactone, polylactic acid, poly-L-lactic acid, mineral oil, etc.

The pharmaceutical composition may be formulated and used in the form of oral formulations such as powders, granules, tablets, capsules, suspensions, emulsions, syrups, aerosols, etc., external preparations, suppositories, and sterile injectable solutions, respectively, according to conventional methods. The form of a carrier may include various amorphous carriers, microspheres, nanofibers, etc.

When formulated, it may be prepared using diluents or excipients such as fillers, extenders, binders, wetting agents, disintegrating agents, surfactants, etc. which are commonly used.

The pharmaceutical composition of the present invention may be administered in various oral or parenteral dosage forms during clinical administration, and is more preferably administered by parenteral methods due to the nature of the viral complex as an active ingredient.

Such solid formulations for oral administration include tablets, pills, powders, granules, capsules, etc. and may be prepared by mixing at least one excipient such as starch, calcium carbonate, sucrose or lactose, gelatin, etc. with the extract and a fraction thereof. In addition, besides simple excipients, lubricants such as magnesium stearate and talc may also be used.

Liquid formulations for oral administration include suspensions, solutions, emulsions, syrups, etc., and various excipients such as wetting agents, sweetening agents, fragrances, preservatives, etc. may be used, in addition to commonly used simple diluents such as water and liquid paraffin.

Formulations for parenteral administration may include sterile aqueous solutions, non-aqueous solvents, suspensions, emulsions, lyophilized formulations, suppositories, etc. As the non-aqueous solvent and suspending agent, propylene glycol, polyethylene glycol, vegetable oil such as olive oil, injectable ester such as ethyl oleate, etc. may be used.

While the content of mesoporous bioactive glass nanoparticles included in the pharmaceutical composition of the present invention is not particularly limited, it can be included at the content of 0.0001 wt. % to 80 wt. %, 0.0001 wt. % to 50 wt. %, and more specifically to 0.01 wt. % to 20 wt. % based on the total weight of the final composition.

Another aspect of the present invention is to provide a method for treating cancer, comprising administering the viral complex or pharmaceutical composition to a subject in which a cancer disease has occurred overexpressing EpCAM.

Here, the terms "cancer disease", "viral complex", and "treatment" are as described above.

Since the pharmaceutical composition of the present invention exhibits a preventive or therapeutic effect of cancer disease in which EpCAM is overexpressed, the treatment method of cancer by the present invention comprising administering this to a subject can be effectively utilized in the treatment of cancer diseases.

As used herein, the term "administration" refers to any activity of introducing the viral complex or pharmaceutical composition to a subject in a suitable manner.

As used herein, the term "subject" refers to all animals including rats, mice, livestock, etc. that may or is likely to have cancer disease, and may be, for example, mammals including humans as a specific example, but is not limited thereto.

The pharmaceutical composition of the present invention may be administered in a pharmaceutically effective amount, and as used herein, the term "pharmaceutically effective amount" refers to an amount sufficient to treat or prevent a disease at a reasonable benefit/risk ratio applicable to medical treatment or prevention. Effective dose levels may be determined by the severity of the disease, activity of the drug, age, weight, health, gender of the patient, the sensitivity to the drug of the patient, administration time of the used composition of the present invention, administration route, the rate of release, duration of the treatment, factors including drugs used in combination or concurrent use with the used composition, and other factors well known in the medical field. The pharmaceutical composition of the present invention may be administered alone or in combination with known therapeutic agents. It is important to consider all the above factors to administer an amount that can obtain the maximum effect in a minimum amount without side effects.

While the pharmaceutical composition of the present invention can be administered by various methods such as oral, intravenous, subcutaneous, intradermal, nasal, intraperitoneal, intramuscular, transdermal, etc., it is more preferable to administer by parenteral method due to the nature of the viral complex as an active ingredient, and its administration amount can vary depending on the age, gender, and weight of the patient and can be readily determined by those skilled in the art.

In addition, the administration amount of the pharmaceutical composition may be determined by those skilled in the art by considering the purpose of use, the severity of disease, age of the patient, weight, gender, history, the type of substance used as an active ingredient, etc. For example, the pharmaceutical composition of the present invention can be administered at 1 mg/kg to 200 mg/kg per adult, specifically, 1 mg/kg to 100 mg/kg, and more specifically, 20 mg/kg to 40 mg/kg, and while the frequency of administration of the pharmaceutical composition is not particularly limited, it may be administered once a day or several times in divided doses. The administration amount does not limit the scope of the invention in any aspect.

In addition, the administration amount of the pharmaceutical composition may be adjusted such that the viral complex of the present invention is administered at 80 mg/kg to 120 mg/kg, and more specifically 100 mg/kg, but is not limited thereto.

Advantageous Effect

While the anti-EpCAM antibody-AAV2/shEGFR complex provided by the present invention does not induce an immune response in vivo, it significantly reduces the expression level of EGFR in tumor cells overexpressing EpCAM and can induce the death of tumor cells, and thus it can be widely utilized in more effective and safe anticancer treatment.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 1 is a schematic diagram showing the preparation process of the anti-EpCAM antibody-AAV2/shEGFR complex provided in the present invention and the active effect for EpCAM-overexpressing tumor cells.

FIG. 2A is a schematic diagram showing the form of shEGFR (SEQ ID NO:5) expressed in cells.

FIG. 2B is a schematic diagram showing the synthetic process of recombinant vector pAAV/shEGFR.

FIG. 3A is a Western blot analysis image showing the results of verifying the synthesis of the recombinant virus bound with streptavidin.

FIG. 3B is a transmission electron micrograph image capturing the shapes of the recombinant AAV2 virus and the anti-EpCAM antibody-AAV2 complex provided in the present invention, and the left side shows recombinant AAV2 virus, and the right side shows an anti-EpCAM antibody-AAV2 complex.

FIG. 4A is a diagram showing the results of comparing the expression levels of mCherry which is a red fluorescent protein expressed in an infected cell line through FACS analysis, after infecting an EpCAM-positive OVCAR3 cell line and an EpCAM-negative A2780 cell line with an anti-EpCAM antibody-AAV2/mCh complex.

FIG. 4B is a diagram showing the results of comparing the expression levels of mCherry which is a red fluorescent protein expressed in an infected cell line, through FACS analysis after infecting an EpCAM-positive OVCAR3 cell line that was pretreated or not pretreated with thyroglobulin with an anti-EpCAM antibody-AAV2/mCh complex.

FIG. 4C is an image of the expression levels of mCherry which is a red fluorescent protein expressed in an infected cell line obtained by a confocal microscope, after infecting an EpCAM-positive OVCAR3 cell line with a recombinant virus AAV2/mCh or anti-EpCAM antibody-AAV2/mCh complex.

FIG. 5A is a Western blood analysis image and a quantitative graph showing the results of measuring the protein levels of EGFR expressed in an OVCAR3 cell line treated with anti-EpCAM antibody-AAV2 complex (Ab-AAV2/shEGFR), scrambled anti-EpCAM antibody-AAV2/scEGFR complex (Ab-AAV2/scEGFR), and DOPC liposome (DOPC/siEGFR) loaded with chemically synthesized EGFR siRNA.

FIG. 5B is a graph showing the results of measuring the mRNA levels of EGFR expressed in an OVCAR3 cell line treated with anti-EpCAM antibody-AAV2 complex (Ab-AAV2/shEGFR), scrambled anti-EpCAM antibody-AAV2/scEGFR complex (Ab-AAV2/scEGFR), and DOPC liposome (DOPC/siEGFR) loaded with chemically synthesized EGFR siRNA.

FIG. 5C is an image and a quantitative graph showing the results of comparing the number of colonies formed by culturing an OVCAR3 cell line treated with anti-EpCAM antibody (EpCAM Ab), scrambled anti-EpCAM antibody-AAV2/scEGFR complex (Ab-AAV2/scEGFR), anti-EpCAM antibody-AAV2 complex (Ab-AAV2/shEGFR) prepared in Example 2, and DOPC liposome (DOPC/siEGFR) loaded with EGFR siRNA that is chemically synthesized.

FIG. 5D is a diagram and a quantitative graph showing the results of measuring the level of apoptosis of an OVCAR3 cell line treated with an anti-EpCAM antibody-AAV2 complex (Ab-AAV2/shEGFR) and a scrambled anti-EpCAM antibody-AAV2/scEGFR complex (Ab-AAV2/scEGFR) through FACS analysis.

FIG. 6A is a fluorescence image and a quantitative graph showing the results of the targeting level in vivo of scrambled AAV2/scEGFR recombinant virus (Cy5.5-AAV2) that was fluorescently labeled with Cy5.5 and a scrambled anti-EpCAM antibody-AAV2/scEGFR complex (Cy5.5-Ab-AAV2) that was fluorescently labeled.

FIG. 6B is a graph showing the results of comparing the levels of TNF-α and INF-γ in order to analyze the inducing effect of immune response, in an immunodeficient animal model administered with recombinant virus (AAV2/shEGFR) or a complex (Ab-AAV2/shEGFR).

FIG. 6C is a graph showing the results of comparing the level of TNF-α in order to analyze the inducing effect of immune responses, in human-derived PBMC administered with recombinant virus (AAV2/shEGFR), a complex (Ab-AAV2/shEGFR), or LPS.

FIG. 7A is a graph showing changes in the volume and weight of tumor tissue depending on a lapse of time, in an animal model administered with recombinant virus (AAV2/shEGFR), a complex (Ab-AAV2/shEGFR), a comparative complex (Ab-AAV2/scEGFR), and DOPC liposome (DOPC/siEGFR) once every 1 week.

FIG. 7B is a graph showing the results of analyzing changes in the volume and weight of tumor tissue depending on a lapse of time, in an animal model administered with a complex (Ab-AAV2/shEGFR) and DOPC liposome (DOPC/siEGFR) once every 2 weeks.

FIG. 7C is an image showing the results of observing by the naked eye the volume of tumor sites of an animal model administered with recombinant virus (AAV2/shEGFR), a complex (Ab-AAV2/shEGFR), a comparative complex (Ab-AAV2/scEGFR), and DOPC liposome (DOPC/siEGFR) once every 1 week, and of an animal model administered with a complex (Ab-AAV2/shEGFR) and DOPC liposome (DOPC/siEGFR) once every 2 weeks.

FIG. 7D is a fluorescent microscope image showing the results of performing TUNEL analysis on each tumor tissue extracted from an animal model administered with recombinant virus (AAV2/shEGFR), a complex (Ab-AAV2/shEGFR), a comparative complex (Ab-AAV2/scEGFR), and DOPC liposome (DOPC/siEGFR) once every 1 week, and from an animal model administered with a complex (Ab-AAV2/shEGFR) and DOPC liposome (DOPC/siEGFR) once every 2 weeks.

FIG. 7E is a graph showing the results of quantitatively analyzing mRNA levels of EGFR expressed in each tumor tissue extracted from an animal model administered with recombinant virus (AAV2/shEGFR), a complex (Ab-AAV2/shEGFR), a comparative complex (Ab-AAV2/scEGFR), and DOPC liposome (DOPC/siEGFR) once every 1 week, and from an animal model administered with a complex (Ab-AAV2/shEGFR) and DOPC liposome (DOPC/siEGFR) once every 2 weeks.

FIG. 7F is an Western blot image and a quantitative graph showing the results of analyzing protein levels of EGFR expressed in each tumor tissue extracted from an animal model administered with recombinant virus (AAV2/shEGFR), a complex (Ab-AAV2/shEGFR), a comparative complex (Ab-AAV2/scEGFR), and DOPC liposome (DOPC/siEGFR) once every 1 week, and from an animal model administered with a complex (Ab-AAV2/shEGFR) and DOPC liposome (DOPC/siEGFR) once every 2 weeks.

FIG. 7G is a confocal microscope image showing the results of confirming through immunostaining intracellular levels of EGFR expressed in each tumor tissue extracted from an animal model administered with recombinant virus (AAV2/shEGFR), a complex (Ab-AAV2/shEGFR), a comparative complex (Ab-AAV2/scEGFR), and DOPC liposome (DOPC/siEGFR) once every 1 week, and from an animal model administered with a complex (Ab-AAV2/shEGFR) and DOPC liposome (DOPC/siEGFR) once every 2 weeks.

DETAILED DESCRIPTION

Hereinafter, the present invention will be described in more detail with reference to examples. However, these examples are for illustrative purposes only and the scope of the present invention is not limited to these examples.

Example 1: Construction of Recombinant Vector and Recombinant Virus for EGFR shRNA Expression The present inventors inserted dsDNA oligomer (shEGFR) consisting of SEQ ID NOs.: 1 and 2 into pSicoR plasmid (Addgene, UK) using Hpal-Xhol restriction site to obtain recombinant vector pSicoR/shEGFR. Here, the underlined sequence in SEQ ID NOs.: 1 and 2 represents the sense and antisense sequence for the EGFR gene (NM_005228.3), and both ends include the Hpal-Xhol restriction site. When the dsDNA oligomer (shEGFR) is expressed intracellularly, it has a small hairpin structure (FIG. 2a). FIG. 2a is a schematic diagram showing the shape of shEGFR expressed in the cell.

```
                                        (SEQ ID NO.: 1)
5'-GTTAAC(GGCACGAGTAACAAGCTCA)TTCAAGAGA(TGAGCTTGTT

ACTCGTGCC)TTTTTCTCGAG-3'

(SEQ ID NO.: 2)
5'-CTCGAGAAAAA(GGCACGAGTAACAAGCTCA)TCTCTTGAA(TGAGC

TTGTTACTCGTGCC)GTTAAC-3'
```

The pSicoR/shEGFR was treated with Xbal-HindIII restriction enzyme to obtain a U6 promoter-driven shEGFR expression cassette fragment, and the expression cassette fragment was inserted into an inverted terminal repeat (ITR) sequence in pAAV-MCS (Stratagene, US) plasmid, to obtain recombinant vector pAAV/shEGFR (FIG. 2b). FIG. 2b is a schematic diagram showing the synthetic process of recombinant vector pAAV/shEGFR. As shown in FIG. 2b, shEGFR expression cassette regulated by U6 promoter is to be located between the two ITR sequences.

The obtained pAAV/shEGFR together with the pHelper plasmid was introduced into 293 cells to prepare recombinant AAV2 virus. The prepared recombinant AAV2 virus was purified by gradient ultracentrifugation, and the titer of the purified virus was measured using a QuickTiter AAV quantitation Kit (Cell Biolabs), and it was confirmed that the measured titer was $4.0 \times 10^{11}$ GC/mL.

Example 2: Construction of Complex Combining Anti-EpCAM Antibody and Recombinant Virus First, $1 \times 10^{11}$ particles of the recombinant virus constructed in Example 1 above was applied to a Streptavidin Conjugation Kit (ab102921, Abcam) to obtain a recombinant virus to which streptavidin was bound. Roughly, the recombinant virus was added to 50 mM amine-free PBS buffer (pH 7.0) containing sulfo NHS-streptavidin included in the kit, and reacted with gentle stirring for 4 hours, thereby obtaining streptavidin-coupled recombinant virus.

Here, the ratio of streptavidin/capsid proteins was maintained at 1:10. Next, after adding a quencher reagent included in the kit, streptavidin that was not bound was removed by centrifugation using centricon. The prepared streptavidin-coupled recombinant virus was confirmed by immunoblot analysis using biotinylated peroxidase (Biotin-HRP, Thermo Fisher Scientific) (FIG. 3a).

FIG. 3a is a Western blot analysis image showing the results of verifying the synthesis of streptavidin-coupled recombinant virus.

10 μg of biotin-bound anti-EpCAM antibody (ab79079, Abcam) was added to $1\times10^{11}$ particles of the obtained streptavidin-coupled recombinant virus and reacted for 24 hours, and an anti-EpCAM antibody-AAV2 complex was prepared thereby. Here, the mixing ratio of the antibody to the virus was set to be 2:10 (molar ratio), and the prepared complex was concentrated using the centrifugal separation method using centricon.

The prepared complex was applied to a transmission electron microscope to analyze the shape of the complex (FIG. 3b).

FIG. 3b is a transmission electron microscope image capturing the shape of the recombinant AAV2 virus and the anti-EpCAM antibody-AAV2 complex provided in the present invention, and the left side shows the recombinant AAV2 virus, and the right side shows the anti-EpCAM antibody-AAV2 complex.

As shown in FIG. 3b, it was confirmed that the recombinant AAV2 virus and the anti-EpCAM antibody-AAV2 complex showed insignificant difference in shape and size. Therefore, binding of the anti-EpCAM antibody to the recombinant AAV2 virus did not affect the morphology and function of the recombinant AAV2 virus.

Example 3: Characteristic Analysis of Cancer Cell Targeting of Anti-EpCAM Antibody-AAV2 Complex Among various ovarian cancer cell lines, the infection efficiency of AAV2 coupled with anti-EpCAM antibody was compared using the FACS analysis, for EpCAM-positive OVCAR3 cell line and the EpCAM-negative A2780 cell line.

First, except that a nucleotide encoding mCherry, which is a red fluorescent protein, was used instead of a nucleotide encoding shEGFR, an anti-EpCAM antibody-AAV2/mCh complex was prepared by performing the same methods in Examples 1 and 2 above.

Next, after the anti-EpCAM antibody-AAV2/mCh complex was inoculated into an OVCAR3 cell line or A2780 cell line, respectively and infected for 4 hours, each cell was washed and cultured for 68 hours. After incubation was completed, the expression level of mCherry was measured in each cell using the FACS analysis method (FIG. 4a). Here, as a control group, an OVCAR3 cell line or an A2780 cell line not inoculated with the anti-EpCAM antibody-AAV2/mCh complex was used.

FIG. 4a is a diagram showing the results of comparing the expression levels of mCherry which is a red fluorescent protein expressed in an infected cell line through FACS analysis, after infecting an EpCAM-positive OVCAR3 cell line and an EpCAM-negative A2780 cell line with an anti-EpCAM antibody-AAV2/mCh complex.

As shown in FIG. 4a, while the expression level of mCherry was shown to be 63.5% in the EpCAM-positive OVCAR3 cell line, it was confirmed that the expression level of mCherry was merely 7.3% in the EpCAM-negative A2780 cell line.

Therefore, the anti-EpCAM antibody-AAV2 complex provided by the present invention was found to have an effect on EpCAM-positive cancer cells.

Example 3-2: Effect of Anti-EpCAM Antibody on the Action of Anti-EpCAM Antibody-AAV2 Complex (I)

In order to confirm the role of the anti-EpCAM antibody in the results obtained in Example 3-1 above, the effect of the anti-EpCAM antibody-AAV2 complex was analyzed depending on the pretreatment of thyroglobulin known to have the same epitope as the epitope of EmCAM recognized by the anti-EpCAM antibody.

Roughly, except for infecting an EpCAM-antibody-AAV2/mCh complex in an EpCAM-positive OVCAR3 cell line that was pretreated or untreated with 500 μg/mL of thyrologubin, the expression level of mCherry was analyzed by performing the same method as in Example 3-1 above (FIG. 4b).

FIG. 4b is a diagram showing the results of comparing the expression levels of mCherry which is a red fluorescent protein expressed in an infected cell line, through FACS analysis after infecting an EpCAM-positive OVCAR3 cell line that was pretreated or not pretreated with thyroglobulin with an anti-EpCAM antibody-AAV2/mCh complex.

As shown in FIG. 4b, while the expression level of mCherry was shown to be 63.5% in the cell line pretreated with thyroglobulin, it was confirmed that the expression level of mCherry was shown to be 27.1% in the OVCAR3 cell line not pretreated with thyroglobulin. Therefore, it was analyzed that the active effect of the anti-EpCAM antibody-AAV2/mCh complex was dependent on EpCAM expressed in OVCAR3 cell line.

Example 3-3: Effect of Anti-EpCAM Antibody on the Action of Anti-EpCAM Antibody AAV2 Complex (II)

In order to verify the role of the anti-EpCAM antibody confirmed in Example 3-2 above, immunostaining analysis was performed.

Roughly, except that a nucleotide encoding mCherry, which is a red fluorescent protein, instead of a nucleotide encoding shEGFR, recombinant virus AAV2/mCh and an anti-EpCAM antibody-AAV2/mCh complex was prepared, by performing the same method in Examples 1 and 2, respectively. Next, after the prepared AAV2/mCh and anti-EpCAM antibody-AAV2/mCh complex were applied to $1\times10^{10}$ GC/mL of an OVCAR3 cell line and infected for 4 hours, each cell was washed and cultured for 68 hours. After the incubation was finished, each cell was photographed with a confocal microscope (FIG. 4c). Here, counterstaining was performed using DAPI.

FIG. 4c is an image of the expression levels of mCherry which is a red fluorescent protein expressed in an infected cell line obtained by a confocal microscope, after infecting an EpCAM-positive OVCAR3 cell line with a recombinant virus AAV2/mCh or anti-EpCAM antibody-AAV2/mCh complex.

As shown in FIG. 4c, whereas mCherry protein fluorescence was strongly observed in cell lines infected with the anti-EpCAM antibody-AAV2/mCh complex, it was confirmed that mCherry protein fluorescence was weakly observed in cell lines infected with native AAV2/mCh virus.

Therefore, it was found that the infection of AAV2 virus was effectively carried out due to the interaction between the anti-EpCAM antibody and the EpCAM protein expressed on the cell surface of OVCAR3.

Example 4: Effect Analysis of Anti-EpCAM Antibody-AAV2/shEGFR Complex at the Cellular Level The anti-EpCAM antibody-AAV2 complex, scrambled anti-EpCAM antibody-AAV2/scEGFR complex and DOPC liposome loaded with chemically synthesized EGFR siRNA were treated, respectively, in an OVCAR3 cell line cultured in a 6-well plate for 4 hours, and cultured for 68 hours. After the incubation was finished, the cultures were centrifuged to obtain cells, and each of the cells obtained above was crushed to obtain respective cell lysates. For each obtained cell lysate, Western blot analysis was performed using anti-EGFR antibody (A10, Santa Cruz Biotechnology), secondary antibody (HRP-conjugated anti-mouse IgG secondary antibodies; SC-2031, Santa Cruz Biotechnology), and ECL solution (Bio-Rad, US), and the expression levels of EGFR expressed in each cell were compared (FIG. 5a). Here, as a control group, an OVCAR3 cell line treated with only PBS was used, and as an internal control group upon Western blot analysis, (3-actin was used.

FIG. 5a is a Western blood analysis image and a quantitative graph showing the results of measuring the protein levels of EGFR expressed in an OVCAR3 cell line treated with anti-EpCAM antibody-AAV2 complex (Ab-AAV2/shEGFR), scrambled anti-EpCAM antibody-AAV2/scEGFR complex (Ab-AAV2/scEGFR), and DOPC liposome (DOPC/siEGFR) loaded with chemically synthesized EGFR siRNA.

As shown in FIG. 5a, when treated with Ab-AAV2/scEGFR compared to the control group, the level of EGFR was somewhat reduced, but the level of EGFR was significantly reduced when treated with Ab-AAV2/shEGFR and DOPC/siEGFR. In particular, it was confirmed that when Ab-AAV2/shEGFR was treated, the lowest level of EGFR (31-39% compared to the control group) was shown.

Example 4-2: Reduction Effect of EGFR mRNA Level

The total RNA of each cell in each cell lysate obtained in Example 4-1 was extracted by applying Rneasy mini kit (Qiagen, US), and the extracted total RNA was applied with TOPscript cDNA synthesis kit (Enzynomics, Korea) to synthesize each cDNA. qRT-PCR was performed using the synthesized cDNA, primers specific to EGFR gene (SEQ ID Nos.: 3 and 4), and StepOne qRT-PCR system (Thermo Fisher Scientific), to compare the level of mRNA of EGFR expressed in each cell (FIG. 5b). Here, as an internal control group, (3-actin was used.

(SEQ ID NO.: 3)
EGFRF: 5'-TGCCCATGAGAAATTTACAGG-3'

(SEQ ID NO.: 4)
EGFRR: 5'-ATGTTGCTGAGAAAGTCACTGC-3'

FIG. 5b is a graph showing the results of measuring the mRNA levels of EGFR expressed in an OVCAR3 cell line treated with anti-EpCAM antibody-AAV2 complex (Ab-AAV2/shEGFR), scrambled anti-EpCAM antibody-AAV2/scEGFR complex (Ab-AAV2/scEGFR), and DOPC liposome (DOPC/siEGFR) loaded with chemically synthesized EGFR siRNA.

As shown in FIG. 5b, when treated with Ab-AAV2/scEGFR compared to the control group, the level of mRNA of EGFR did not change, but when treated with Ab-AAV2/shEGFR and DOPC/siEGFR, the mRNA of EGFR was reduced. In particular, when treated with Ab-AAV2/shEGFR, it was confirmed that the lowest mRNA level of EGFR was shown.

Example 4-3: Inhibitory Effect on Colony Formation

The effect of the expression suppression of EGFR on the colony formation of cells was analyzed in an OVCAR3 cell line infected with the anti-EpCAM antibody-AAV2/shEGFR complex.

Roughly, after incubating an OVCAR3 cell line cultured in a 6-well plate for 24 hours, an anti-EpCAM antibody, scrambled anti-EpCAM antibody-AAV2/scEGFR complex, an anti-EpCAM antibody-AAV2 complex prepared in Example 2, and DOPC liposome loaded with chemically synthesized EGFR siRNA were treated for 4 hours, respectively, and cultured for 68 hours. After the incubation was finished, each cell was fixed by treatment with 4% (v/v) paraformaldehyde and stained with 0.5% (w/v) crystal violet solution, and stained colonies were counted using a Minibis Bioimaging system (DNR Bio-Imaging Systems Ltd., Israel) (FIG. 5c). Here, as a control group, an OVCAR3 cell line treated with only PBS was used.

FIG. 5c is an image and a quantitative graph showing the results of comparing the number of colonies formed by culturing an OVCAR3 cell line treated with anti-EpCAM antibody (EpCAM Ab), scrambled anti-EpCAM antibody-AAV2/scEGFR complex (Ab-AAV2/scEGFR), anti-EpCAM antibody-AAV2 complex (Ab-AAV2/shEGFR) prepared in Example 2, and DOPC liposome (DOPC/siEGFR) loaded with EGFR siRNA that is chemically synthesized.

As shown in FIG. 5c, EpCAM Ab and Ab-AAV2/scEGFR did not show any significant difference, but Ab-AAV2/shEGFR and DOPC-siEGFR showed significantly lower colony levels than the control group. In particular, it was confirmed that Ab-AAV2/shEGFR showed the lowest colony level (about 29.5% compared to the control group).

Therefore, when the anti-EpCAM antibody-AAV2/shEGFR complex was used, it was analyzed to induce the inhibition of EGFR expression, thereby suppressing anchorage-dependent colonogenicity in an OVCAR3 cell line.

Example 4-4: Apoptosis Induction Effect

The effect of the expression inhibition of EGFR on apoptosis was analyzed in an OVCAR3 cell line infected with the anti-EpCAM antibody-AAV2/shEGFR complex.

Roughly, after treating $1 \times 10^{10}$ GC/mL of an anti-EpCAM antibody-AAV2 complex prepared in Example 2, or a scrambled anti-EpCAM antibody-AAV2/scEGFR complex was treated in $5 \times 10^5$ OVCAR3 cells for 4 hours, respectively, and cultured for 68 hours. After the incubation was finished, the culture was centrifuged to obtain each cell, and the obtained cells were stained with propidium iodide and FITC-labeled Annexin-V, and analyzed by Guava easyCyte flow cytometry system (FIG. 5d). Here, an OVCAR3 cell line treated with only PBS was used as a control group.

FIG. 5d is a diagram and a quantitative graph showing the results of measuring the level of apoptosis of an OVCAR3 cell line treated with an anti-EpCAM antibody-AAV2 complex (Ab-AAV2/shEGFR) and a scrambled anti-EpCAM antibody-AAV2/scEGFR complex (Ab-AAV2/scEGFR) through FACS analysis.

As shown in FIG. 5d, in the control group and Ab-AAV2/scEGFR, cells that were killed were not detected, but in the case of Ab-AAV2/shEGFR, it was confirmed that cell death was increased by 87.4%, and the necrotic cell death was increased by 8.6%. Therefore, when the anti-EpCAM antibody-AAV2/shEGFR complex was used, it was analyzed to induce the inhibition of EGFR expression, thereby inducing apoptosis in an OVCAR3 cell line.

Example 5: Analysis of Effect of Anti-EpCAM Antibody-AAV2/shEGFR Complex in Animal Model An OVCAR3 cell line ($1\times10^8$) which is an EpCAM-positive ovarian cancer cell line, was implanted into the left though of a 5-week-old female BALB/c nude mouse, and the mouse was raised until the volume of cancer tissue reached 200 mm$^3$.

Fluorescent substance (Cy5.5, 0.5 µg), scrambled AAV2/scEGFR recombinant virus fluorescently labeled with Cy5.5 (Cy5.5-AAV2, $1\times10^{12}$ GC/mL), or a scrambled anti-EpCAM antibody-AAV2/scEGFR complex (Cy5.5-Ab-AAV2, $1\times10^{12}$ GC/mL) fluorescently labeled with Cy5.5 was injected intravenously through the tail vein of the mouse. At time points after 4 hours and 24 hours, major organs (liver, spleen, kidney, heart, and lung) and tumor tissue were extracted, and each extracted organ and tumor tissue was applied to IVIS Spectrum (Caliper Life Science, Inc., USA) to compare the accumulation level of fluorescent labels (FIG. 6A).

FIG. 6a is a fluorescence image and a quantitative graph showing the results of the targeting level in vivo of scrambled AAV2/scEGFR recombinant virus (Cy5.5-AAV2) that was fluorescently labeled with Cy5.5 and a scrambled anti-EpCAM antibody-AAV2/scEGFR complex (Cy5.5-Ab-AAV2) that was fluorescently labeled.

As shown in FIG. 6a, in the cases of the control group (Cy5.5) not bound with an antibody and the recombinant virus (Cy5.5-AAV2), it was detected the most in the liver and then in the kidney, but in the complex bound with the antibody (Cy5.5-Ab-AAV2), it was confirmed to be extracted the most in tumor tissue, and then in the kidney.

In the case of kidney, as it was analyzed that the components that did not remain in the body were to be discharged through urine, it was found that substantially, the control group (Cy5.5) not bound with the antibody and the recombinant virus (Cy5.5-AAV2) accumulated in the liver, and the complex bound with the antibody accumulated in tumor tissue.

The above result showed that the complex (Cy5.5-Ab-AAV2) bound with the antibody was analyzed to be targeted to tumor by the anti-EpCAM antibody to be accumulated in tumor tissue.

Example 5-2: Induction Effect of Immune Response of Anti-EpCAM Antibody-AAV2/shEGFR Complex The recombinant virus (AAV2/shEGFR) prepared in Example 1 above or the complex (Ab-AAV2/shEGFR) prepared in Example 2 above was intravenously injected to a C57BL/6J mouse, which is an immunodeficient animal model, at a level of $1\times10^{12}$ GC/mL per 100 µL of PBS. At time points after 6 hours or 24 hours, blood was collected from the heart of the mouse. The serum obtained from the collected blood was centrifuged to obtain plasma, and the level of TNF-α and the level of INF-γ included in the obtained serum were measured using TNF-α Mouse ELISA Kit (Thermo Fisher Scientific) and INF-γ Mouse ELISA Kit (Thermo Fisher Scientific), and were compared (FIG. 6b).

FIG. 6b is a graph showing the results of comparing the levels of TNF-α and INF-γ in order to analyze the inducing effect of immune response, in an immunodeficient animal model administered with recombinant virus (AAV2/shEGFR) or a complex (Ab-AAV2/shEGFR).

As shown in FIG. 6b, it was confirmed that the levels of TNF-α and INF-γ did not increase significantly in any case.

Therefore, it was analyzed that the anti-EpCAM antibody-AAV2/shEGFR complex did not induce immune response.

Example 5-3: Induction Effect of Immune Response of Anti-EpCAM Antibody-AAV2/shEGFR Complex on Human-Derived Cells According to a known method (standard Ficoll-Paque density-gradient centrifugation method), peripheral blood mononuclear cells (PBMC) were isolated from the human blood, and after seeding the isolated PBMC in a 96-well plate at $1\times10^4$ cells per well, of RPMI 1640 medium (10% PBS, 1% penicillin-streptomycin, 1% L-glutamine included) was added thereto and cultured for 12 hours. After incubation was finished, the recombinant virus (AAV2/shEGFR, $1\times10^{10}$ GC/mL) prepared in Example 1 above, the complex (Ab-AAV2/shEGFR, $1\times10^{10}$ GC/mL) prepared in Example 2 above, or lipopolysaccharide (50 ng/mL) was treated to the PBMC. At time points after 6 hours or 24 hours, the level of TNF-α expressed in the PBMC was measured using TNF-α Mouse ELISA Kit (Thermo Fisher Scientific) (FIG. 6c). Here, as a control group, PBMC treated with PBS was used.

FIG. 6c is a graph showing the results of comparing the level of TNF-α in order to analyze the inducing effect of immune responses, in human-derived PBMC administered with recombinant virus (AAV2/shEGFR), a complex (Ab-AAV2/shEGFR), or LPS.

As shown in FIG. 6c, cases of AAV2/shEGFR and Ab-AAV2/shEGFR did not show significance difference with the control group, but when LPS was treated, it was confirmed that a significantly high level of TNF-α was detected.

Therefore, it was analyzed that the anti-EpCAM antibody-AAV2/shEGFR complex did not induce immune response in humans as well as in mice.

Example 6: Analysis of Anticancer Effect of Anti-EpCAM Antibody-AAV2/shEGFR Complex in Animal Model

Example 6-1: Changes in Tumor Volume In Vivo Depending on Administration of Anti-EpCAM Antibody-AAV2/shEGFR Complex (I)

After implanting an OVCAR3 cell line ($1\times10^8$) in the left thigh of a 5-week-old female BALB/c nude mouse, it was rinsed until the volume of cancer tissue reached 200 mm$^3$.

The mouse was raised by intravenously injecting 5 times at an interval of 1 week for 5 weeks through the tail vein of the mouse a scrambled anti-EpCAM antibody-AAV2/scEGFR complex (Ab-AAV2/scEGFR, $1 \times 10^{12}$ GC/mL), the recombinant virus (AAV2/shEGFR, $1 \times 10^{10}$ GC/mL) prepared in Example 1 above, the complex (Ab-AAV2/shEGFR, $1 \times 10^{10}$ GC/mL) prepared in Example 2 above, or DOPC liposome loaded with chemically synthesized EGFR siRNA (DOPC/siEGFR, 4 μg). The volume and weight change of tumor tissue depending on the lapse of breeding period were analyzed (FIG. 7a). Here, as a control group, a mouse administered with PBS was used.

FIG. 7a is a graph showing changes in the volume and weight of tumor tissue depending on a lapse of time, in an animal model administered with recombinant virus (AAV2/shEGFR), a complex (Ab-AAV2/shEGFR), a comparative complex (Ab-AAV2/scEGFR), and DOPC liposome (DOPC/siEGFR) once every 1 week.

As shown in FIG. 7a, unlike the control group, the volume and weight of tumor were reduced depending on the lapse of time only in the cases of Ab-AAV2/shEGFR and DOPC-siEGFR, and it was confirmed that the volume and weight of tumor decreased at the highest level in the case of Ab-AAV2/shEGFR, which was more than DOPC/siEGFR.

Example 6-2: Changes in Tumor Volume In Vivo Depending on Administration of Anti-EpCAM Antibody-AAV2/shEGFR Complex Except that the complex prepared in Example 2 above (Ab-AAV2/shEGFR, $1 \times 10^{10}$ GC/mL) or DOPC liposome loaded with chemically synthesized EGFR siRNA (DOPC/siEGFR, 4 μg) was intravenously injected 3 times at an interval of 2 weeks through the tail vein of the mouse, using the same method as Example 6-1 above, the volume and weight changes of tumor tissue were analyzed depending on the lapse of breeding period (FIG. 7b).

FIG. 7b is a graph showing the results of analyzing changes in the volume and weight of tumor tissue depending on a lapse of time, in an animal model administered with a complex (Ab-AAV2/shEGFR) and DOPC liposome (DOPC/siEGFR) once every 2 weeks.

As shown in FIG. 7b, unlike the results of FIG. 7a, it was confirmed that the volume and weight of tumor decreased depending on the lapse of time only in the case of Ab-AAV2/shEGFR.

Example 6-3: Volume Change of Tumor

After the final intravenous injection in Examples 6-1 and 6-2 above, at a time point after 1 week, the volumes of the tumor implant site of each mouse were compared by observing with the naked eye (FIG. 7c).

FIG. 7c is an image showing the results of observing by the naked eye the volume of tumor sites of an animal model administered with recombinant virus (AAV2/shEGFR), a complex (Ab-AAV2/shEGFR), a comparative complex (Ab-AAV2/scEGFR), and DOPC liposome (DOPC/siEGFR) once every 1 week, and of an animal model administered with a complex (Ab-AAV2/shEGFR) and DOPC liposome (DOPC/siEGFR) once every 2 weeks.

As shown in FIG. 7c, the volume of tumor cells significantly decreased only in the cases of Ab-AAV2/shEGFR and DOPC-siEGFR in animal models administered once per 1 week, and it was confirmed that the volume of tumor cells significantly decreased only in the case of Ab-AAV2/shEGFR in an animal model administered once every 2 weeks.

Example 6-4: TUNEL Analysis

After the final intravenous injection in Examples 6-1 and 6-2 above, at a time point after 1 week, tumor tissue was extracted from each mouse, and in order to confirm that apoptosis occurred in each extracted tumor tissue, TUNEL analysis was performed (FIG. 7d).

FIG. 7d is a fluorescent microscope image showing the results of performing TUNEL analysis on each tumor tissue extracted from an animal model administered with recombinant virus (AAV2/shEGFR), a complex (Ab-AAV2/shEGFR), a comparative complex (Ab-AAV2/scEGFR), and DOPC liposome (DOPC/siEGFR) once every 1 week, and from an animal model administered with a complex (Ab-AAV2/shEGFR) and DOPC liposome (DOPC/siEGFR) once every 2 weeks.

As shown in FIG. 7b, apoptosis of tumor cells occurred only in the case of Ab-AAV2/shEGFR and DOPC-siEGFR in an animal model administered once every 1 week, and it was confirmed that apoptosis of tumor cells occurred only in the case of Ab-AAV2/shEGFR in an animal model administered once every 2 weeks.

Therefore, it was found that the anti-EpCAM antibody-AAV2/shEGFR complex provided in the present invention induced apoptosis of tumor cells in vivo.

Example 6-5: qRT-PCR Analysis

After the final intravenous injection in Examples 6-1 and 6-2 above, at a time point after 1 week, tumor tissue was extracted from each mouse, and the mRNA level of EGFR expressed in the extracted tumor tissue was analyzed by the qRT-PCR analysis method carried out in Example 4-2.

FIG. 7e is a graph showing the results of quantitatively analyzing mRNA levels of EGFR expressed in each tumor tissue extracted from an animal model administered with recombinant virus (AAV2/shEGFR), a complex (Ab-AAV2/shEGFR), a comparative complex (Ab-AAV2/scEGFR), and DOPC liposome (DOPC/siEGFR) once every 1 week, and from an animal model administered with a complex (Ab-AAV2/shEGFR) and DOPC liposome (DOPC/siEGFR) once every 2 weeks.

As shown in FIG. 7e, it was confirmed that mRNA of EGFR was detected at the lowest level in the case of administering Ab-AAV2/shEGFR in all animals administered once every 1 week and once every 2 weeks.

Example 6-6: Western Blot Analysis

After the final administration of Examples 6-1 and 6-2 above, at a time point after 1 week, tumor tissue was extracted from each mouse, and the protein level of EGFR expressed in the extracted tumor tissue was analyzed by the Western blot analysis method carried out in Example 4-1.

FIG. 7f is an Western blot image and a quantitative graph showing the results of analyzing protein levels of EGFR expressed in each tumor tissue extracted from an animal model administered with recombinant virus (AAV2/shEGFR), a complex (Ab-AAV2/shEGFR), a comparative complex (Ab-AAV2/scEGFR), and DOPC liposome (DOPC/siEGFR) once every 1 week, and from an animal model administered with a complex (Ab-AAV2/shEGFR) and DOPC liposome (DOPC/siEGFR) once every 2 weeks.

As shown in FIG. 7f, it was confirmed that the EGFR protein was detected at the lowest level in the case of administering Ab-AAV2/shEGFR in all animals administered once every 1 week and once every 2 weeks.

Example 6-7: Immunostaining Analysis

After the final intravenous administration in Examples 6-1 and 6-2 above, at a time point after 1 week, tumor tissue was extracted from each mouse, and the extracted tumor tissue was immunostained by the immunohistochemistry (IHC) staining method.

Roughly, the extracted tissue was fixed by applying 10% formalin for 24 hours, and it was embedded in a paraffin block, tumor tissue slices having a thickness of 6 μm were obtained. The obtained tumor tissue slices were washed with DPBS buffer containing Triton X-100 (0.0125%), and blocked by adding DPBS buffer containing 1% BSA. Next, the slices were treated with anti-EGFR antibody (A10) and reacted for 12 hours, and after applying a secondary antibody coupled with biotin and reacting for 30 minutes, they were washed with DPBS buffer. Finally, Vectastain ABC Reagent was applied to the slices, and after reacting for 20 minutes, color development was achieved by treatment with 3,3'-diaminobenzidine (DAB) (FIG. 7g).

As shown in FIG. 7g, it was confirmed that the level of intracellular EGFR was lowest when Ab-AAV2/shEGFR was administered in all animals administered once per 1 week and once every 2 week.

To summarize the results of Examples 6-1 to 6-7, the anti-EpCAM antibody-AAV2/shEGFR complex provided in the present invention specifically acts on tumor cells expressing EpCAM existing in vivo, thereby reducing the level of intracellular EGFR, and accordingly, it was known to have effect of killing tumor cells thereby.

Therefore, it was analyzed that the anti-EpCAM antibody-AAV2/shEGFR complex can be used as an anticancer agent that specifically acts on tumor cells expressing EpCAM.

From the above description, those skilled in the art will appreciate that the present invention can be implemented in other specific forms without changing the technical spirit or essential features. In this regard, the embodiments described above are to be understood in all respects as illustrative and not restrictive. The scope of the present invention should be construed that all changes or modifications derived from the meaning and scope of the following claims and equivalent concepts rather than the detailed description are included in the scope of the present invention.

The invention claimed is:

1. A viral complex, comprising:
   an adeno-associated viral vector capable of delivering shRNA that suppresses an expression of epidermal growth factor receptor (EGFR) in a cell and;
   an anti-epithelial cell adhesion molecule (EpCAM) antibody conjugated to the viral vector.

2. The viral complex of claim 1, wherein the shRNA is double-strand DNA (dsDNA) consisting of SEQ ID NOs.: 1 and 2.

3. The viral complex of claim 1, wherein the viral complex does not induce an immune response in vivo.

4. A method for treating a cancer, comprising administering the viral complex of claim 1 to a subject excluding a human, the cancer is associated with overexpression of EpCAM.

5. The method of claim 4, wherein the viral complex specifically acts on a cancer cell overexpressing EpCAM.

6. The method of claim 5, wherein the cancer cell is a cell of cancer tissue selected from the group consisting of pancreatic cancer, breast cancer, prostate cancer, brain tumor, head and neck carcinoma, melanoma, liver cancer, stomach cancer, colon cancer, uterine cancer, ovarian cancer, rectal cancer, esophageal cancer, small intestine cancer, anal muscle cancer, colon cancer, fallopian tube carcinoma, endometrial carcinoma, cervical carcinoma, vaginal carcinoma, vulvar carcinoma, bladder cancer, kidney cancer, ureter cancer, renal cell carcinoma, renal pelvic carcinoma, and a combination thereof.

7. The method of claim 4, wherein the viral complex suppresses an expression of EGFR in a cancer cell by delivering shRNA that suppresses the expression of EGFR in a cancer cell.

* * * * *